(12) United States Patent
Heinrich et al.

(10) Patent No.: US 7,491,810 B2
(45) Date of Patent: Feb. 17, 2009

(54) TRANSGENIC SCREEN AND METHOD FOR SCREENING MODULATORS OF BRAIN-DERIVED NEUROTROPHIC FACTOR (BDNF) PRODUCTION

(75) Inventors: Gerhard Heinrich, Pleasant Hill, CA (US); Gigi Huynh, Vallejo, CA (US)

(73) Assignee: U.S. Department of Veterans Affairs, Washington, DC (US)

( * ) Notice: Subject to any disclaimer, the term of this patent is extended or adjusted under 35 U.S.C. 154(b) by 849 days.

(21) Appl. No.: 10/306,737

(22) Filed: Nov. 29, 2002

(65) Prior Publication Data

US 2003/0149994 A1 Aug. 7, 2003

Related U.S. Application Data

(60) Provisional application No. 60/334,079, filed on Nov. 30, 2001.

(51) Int. Cl.
C07H 21/04 (2006.01)
C12N 5/00 (2006.01)
C12N 5/02 (2006.01)

(52) U.S. Cl. .................. 536/24.1; 536/23.4; 435/325

(58) Field of Classification Search .............. 536/23.1
See application file for complete search history.

(56) References Cited

U.S. PATENT DOCUMENTS

| 5,869,250 | A | * | 2/1999 | Cheng et al. ............... | 435/6 |
| 6,380,458 | B1 |   | 4/2002 | Lin |  |
| 6,465,715 | B1 | * | 10/2002 | Zwaal et al. ............... | 800/13 |
| 6,632,671 | B2 | * | 10/2003 | Unger ...................... | 435/455 |
| 6,673,600 | B2 | * | 1/2004 | Peraus et al. ............. | 435/320.1 |
| 6,689,936 | B1 | * | 2/2004 | Burgeson et al. .......... | 800/3 |

FOREIGN PATENT DOCUMENTS

| EP | 1050309 A1 | 11/2000 |
| JP | 5317049 | 3/1993 |
| JP | 07025777 A | 1/1995 |
| WO | WO 91/03568 | 3/1991 |
| WO | WO 99/38534 | 8/1999 |
| WO | WO 9964586 A2 * | 12/1999 |

OTHER PUBLICATIONS

Zhong TP, Kaphingst K, Akella U, Haldi M, Lander ES, Fishman MC.1998.Zebrafish Genomic Library in Yeast Artificial Chromosomes. Genomics. Feb. 15;48(1):136-8.*

Amemiya CT, Zon LI. 1999.Generation of a zebrafish P1 artificial chromosome library.Genomics. Jun. 1;58(2):211-3.*

Cormack BP, Valdivia RH, Falkow S. FACS—optimized mutants of the green fluorescent protein (GFP). Gene. 1996;173(1 Spec No):33-8.*

Schaefer BC. 1995. Revolutions in rapid amplification of cDNA ends: new strategies for polymerase chain reaction cloning of full-length cDNA ends. Anal Biochem. May 20, 1995;227(2):255-73.*

Alderson, R.F., Alterman, A.L., Barde, Y.A. and Lindsay, R.M., (1990) Brain-derived neurotrophic factor increases survival and differentiated functions of rat septal cholinergic neurons in culture. Neuron, 5: 297-306.

Amgen-Regeneron Partners. (2001) Intrathecal and Subcutaneous BDNF not shown effective in ALS. MDA Research. Web site: http://www.mdausa.org/research/ct-alsbdnf-it.html. (Jan. 11, 2002.).

Balbes, L.M., M. Cline, and D.D. Beusen. (2001) From target to drug in the virtual discovery lab. Drug Discovery and Development. Apr. 2001.

Biffo, S., Dechant, G., Okazawa, H. and Barde, Y.A., (1994) Molecular control of neuronal survival in the chick embryo. EXS, 71:39-48.

Binder, D.K., S. D. Croll, C. M. Gall, and H. E. Scharfman, (2001) BDNF and epilepsy: too much of a good thing? Trends in Neurosciences, 24(1):47-53.

Bishop, J.F., Joshi, G., Mueller, G.P. and Mouradian, M.M., (1997) Localization of putative calcium-responsive regions in the rat BDNF gene. Brain Res Mol Brain Res 50 IP, 1-2:154-164.

Bishop, J.F., Mueller, G.P. and Mouradian, M.M., (1994) Alternate 5' exons in the rat brain-derived neurotrophic factor gene: differential patterns of expression across brain regions. Brain Res Mol Brain Res 26 IP, 1-2:225-232.

Cockett, M., N. Dracopoli, and E. Sigal. (2000) Applied genomics: intergration of the technology within pharmaceutical research and development. Current Opinion in Biotechnology, 11:602-609.

Cohen, N., Abramov, S., Dror, Y., and Freeman, A. (2001) In vitro enzyme evolution: the screening challenge of isolating the one in a million. Trends in Biotechnology, 19(12):507-510.

Davies, A.M., Thoenen, H. and Barde, Y.A., (1986) The response of chick sensory neurons to brain-derived neurotrophic factor. J Neurosci, 6:1897-904.

Dodd, A., P.M.Curtis, L.C Williams, and D.R Love. (2000) Zebrafish: bridging the gap between development and disease. Human Molecular Genetics. 9(16):Review, 2443-2449.

Finkbeiner, S., (2000) Calcium regulation of the brain-derived neurotrophic factor gene. Cell Mol Life Sci 57 IP, 3:394-401.

Fox, S.J., M.A. Yund, and S. Farr-Jones. (2000) Assay innovations vital to improving HTS. Drug Discovery and Development. Mar. 2000.

(Continued)

Primary Examiner—Valarie Bertoglio
(74) Attorney, Agent, or Firm—Dinesh Agarwal, P.C.

(57) ABSTRACT

A transgenic screen and method for screening biological and chemical test substances or molecules for their ability to influence or modulate the production of BDNF in cells, includes a fusion gene having a zebrafish BDNF gene fragment (promoter) and a fluorescent marker gene inserted downstream of the BDNF gene fragment. When the fusion gene is injected into a zebrafish embryo, the BDNF promoter causes the production of fluorescent protein in various cell types. The embryo is exposed to a test substance for determining the effect thereof on the production of the fluorescent marker protein.

6 Claims, 13 Drawing Sheets

OTHER PUBLICATIONS

Frade, J.M., Bovolenta, P., Martinez-Morales, J.R., Arribas, A., Barbas, J.A. and Rodriguez-Tebar, A., (1997) Control of early cell death by BDNF in the chick retina. Development, 124:3313-20.

Gotz, R., Koster, R., Winkler, C., Raulf, F., Lottspeich, F., Schartl, M. and Thoenen, H., (1994) Neurotrophin-6 is a new member of the nerve growth factor family. Nature, 372:266-9.

Guillemot, F., Auffray, C. and Devignes, M.D., (1999) Detailed transcript map of a 810-kb region at 11p14 involving identification of 10 novel human 3' exons. Eur J Hum Genet 7 IP, 4:487-495.

Harvey, K.J., Lukovic, D. and Ucker, D.S., (2001) Membrane-targeted green fluorescent protein reliably and uniquely marks cells through apoptotic death. Cytometry, 43:273-8.

Hashimoto, M. and Heinrich, G., (1997) Brain-derived neurotrophic factor gene expression in the developing zebrafish. Int J Dev Neurosci, 15:983-97.

Haupts, U., M. Rudiger. and A.J. Pope. (2000) Macroscopic versus microscopic fluorescence techniques in (ultra)-high throughput screening. Drug Discovery Today: HTS Supplement, 1 (1). Jun. 2000.

Hayes, V.Y., Towner, M.D. and Isackson, P.J., (1997) Organization, sequence and functional analysis of a mouse BDNF promoter. Brain Res Mol Brain Res 45 IP, 2:189-198.

Herzog, K.H., Bailey, K. and Barde, Y.A., (1994) Expression of the BDNF gene in the developing visual system of the chick. Development, 120:1643-9.

Hyman, C., Hofer, M., Barde, Y.A., Juhasz, M., Yancopoulos, G.D., Squinto, S.P. and Lindsay, R.M., (1991) BDNF is a neurotrophic factor for dopaminergic neurons of the substantia nigra. Nature, 350:230-2.

Huynh, G. and G. Heinrich. (2001) Brain-derived neurotrophic factor gene organization and transcription in the zebrafish embryo. International Journal of Developmental Neuroscience,19:663-673.

Inoue, A., Takahashi, M., Hatta, K., Hotta, Y. and Okamoto, H., (1994) Developmental regulation of islet-1 mRNA expression during neuronal differentiation in embryonic zebrafish. Dev Dyn, 199:1-11.

Ip, N.Y., Ibanez, C.F., Nye, S.H., McClain, J., Jones, P.F., Gies, D.R., Belluscio, L., Le Beau, M.M., Espinosa R, 3.r., Squinto, S.P. and et, a.l., (1992) Mammalian neurotrophin-4: structure, chromosomal localization, tissue distribution, and receptor specificity. Proc Natl Acad Sci U S A, 89:3060-4.

Johnson, J.E., Barde, Y.A., Schwab, M. and Thoenen, H., (1986) Brain-derived neurotrophic factor supports the survival of cultured rat retinal ganglion cells. J Neurosci, 6:3031-8.

Levi-Montalcini, R., Dal Toso, R., della Valle, F., Skaper, S.D. and Leon, A., (1995) Update of the NGF saga. J Neurol Sci, 130:119-27.

Levi-Montalcini, R., (1998) The saga of the nerve growth factor. Neuroreport, 9:R71-83.

Lum, T., G. Huynh, and G. Heinrich. (2001) Brain-derived neurotrophic factor and TrkB tyrosine kinase receptor gene expression in zebrafish embryo and larva. International Journal of Developmental Neuroscience, 19:569-587 (Abstract—2 pages).

Maisonpierre, P.C., Belluscio, L., Squinto, S., Ip, N.Y., Furth, M.E., Lindsay, R.M. and Yancopoulos, G.D., (1990) Neurotrophin-3: a neurotrophic factor related to NGF and BDNF. Science, 247:1446-51.

Maisonpierre, P.C., Le Beau, M.M., Espinosa R, 3.r., Ip, N.Y., Belluscio, L., de la, M.o.S., Squinto, S., Furth, M.E. and Yancopoulos, G.D., (1991) Human and rat brain-derived neurotrophic factor and neurotrophin-3: gene structures, distributions, and chromosomal localizations. Genomics, 10:558-68.

Marmigere, F., Rage, F., Tapia-Arancibia, L. and Arancibia, S., (1998) Expression of mRNAs encoding BDNF and its receptor in adult rat hypothalamus. Neuroreport 9 IP, 6:1159-1163.

Martin, S.C., Sandell, J.H. and Heinrich, G., (1998) Zebrafish TrkC1 and TrkC2 receptors define two different cell populations in the nervous system during the period of axonogenesis. Dev Biol, 195:114-30.

Metsis, M., Timmusk, T., Arenas, E. and Persson, H., (1993) Differential usage of multiple brain-derived neurotrophic factor promoters in the rat brain following neuronal activation. Proc Natl Acad Sci U S A 90 IP, 19:8802-8806.

Nanda, S. and Mack, K.J., (1998) Multiple promoters direct stimulus and temporal specific expression of brain-derived neurotrophic factor in the somatosensory cortex. Brain Res Mol Brain Res 62 IP, 2:216-219.

Nature America Inc. (2000) Targeting zebrafish. nature genetics, 26(2):129-130.

Nasevicius, A., and Ekker, S. (2000) Effective targeted gene 'knockdown' in zebrafish. nature genetics, 26:216-220.

Nilsson, A.S., Fainzilber, M., Falck, P. and Ibanez, C.F., (1998) Neurotrophin-7: a novel member of the neurotrophin family from the zebrafish. FEBS Lett, 424:285-90.

Pickering, L. (2001) Developing Drugs to Counter Disease. Medical Chemistry, 44-47.

Reiss, T. (2001) Drug discovery of the future: the implications of the human genome project. Trends in Biotechnology, 19(12):496-499.

Rodriguez-Tebar, A. and Barde, Y.A., (1988) Binding characteristics of brain-derived neurotrophic factor to its receptors on neurons from the chick embryo. J Neurosci, 8:3337-42.

Rodriguez-Tebar, A., Jeffrey, P.L., Thoenen, H. and Barde, Y.A., (1989) The survival of chick retinal ganglion cells in response to brain-derived neurotrophic factor depends on their embryonic age. Dev Biol, 136:296-303.

Russo-Neustadt A, T. Ha, R. Ramirez, and J.P. Kesslak. (2001) Physical activity antidepressant treatment combination: impact on brain-derived neurotrophic factor and behavior in an animal model.. Behaviour Brain Research, 120(1):87-95. BLTC Research. Web site: http://biopsychiatry.com/bdnf.htm. (Jan. 11, 2002.) (Abstract—2 pages).

Sano, K., Nanba, H., Tabuchi, A., Tsuchiya, T. and Tsuda, M., (1996) BDNF gene can Be activated by Ca2+ signals without involvement of de novo AP-1 synthesis. Biochem Biophys Res Commun 229 IP, 3:788-793.

Sendtner, M., Holtmann, B., Kolbeck, R., Thoenen, H. and Barde, Y.A., (1992) Brain-derived neurotrophic factor prevents the death of motoneurons in newborn rats after nerve section. Nature, 360:757-9.

Shieh, P.B. and Ghosh, A., (1999) Molecular mechanisms underlying activity-dependent regulation of BDNF expression. J Neurobiol 41 IP, 1:127-134.

Shieh, P.B., Hu, S.C., Bobb, K., Timmusk, T. and Ghosh, A., (1998) Identification of a signaling pathway involved in calcium regulation of BDNF expression. Neuron, 20:727-40.

Shintani, A., Ono, Y., Kaisho, Y. and Igarashi, K., (1992) Characterization of the 5'-flanking region of the human brain-derived neurotrophic factor gene. Biochem Biophys Res Commun 182 IP, 1:325-332.

Stainier, D. (2001) Zebrafish Genetics and Vertegrate Heart Formation. Nature Reviews, 2:39-48.

Tao, X., Finkbeiner, S., Arnold, D.B., Shaywitz, A.J. and Greenberg, M.E., (1998) Ca2+ influx regulates BDNF transcription by a CREB family transcription factor-dependent mechanism. Neuron 20 IP, 4:709-726.

Timmusk, T., Belluardo, N., Persson, H. and Metsis, M., (1994a) Developmental regulation of brain-derived neurotrophic factor messenger RNAs transcribed from different promoters in the rat brain. Neuroscience 60 IP, 2:287-291.

Timmusk, T., Lendahl, U., Funakoshi, H., Arenas, E., Persson, H. and Metsis, M., (1995) Identification of brain-derived neurotrophic factor promoter regions mediating tissue-specific, axotomy-, and neuronal activity-induced expression in transgenic mice. J Cell Biol, 128:185-99.

Timmusk, T., Palm, K., Metsis, M., Reintam, T., Paalme, V., Saarma, M. and Persson, H., (1993) Multiple promoters direct tissue-specific expression of the rat BDNF gene. Neuron 10 IP, 3:475-489.

Timmusk, T., Persson, H. and Metsis, M., (1994b) Analysis of transcriptional initiation and translatability of brain-derived neurotrophic factor mRNAs in the rat brain. Neurosci Lett 177 IP, 1-2:27-31.

Vente, A., Korn, B., Zehetner, G., Poustka, A. and Lehrach, H., (1999) Distribution and early development of microarray technology in Europe. Nat Genet, 22:22.

Wixon, J. (2000) Danio rerio, the zebrafish. Yeast, 17:225-231. Web site: http://www.zolodex.com/tests/. (Sep. 19, 2001.).

Zehetner, G. and Lehrach, H., (1994) The Reference Library System—sharing biological material and experimental data. Nature, 367:489-491.

Schug, J., Overton, G.C., (1997) 'TESS: Transcription Element Search Software on the WWW', Technical Report CBIL-TR-1997-1001-v0.0, of the Computational Biology and Informatics Laboratory, School of Medicine, University of Pennsylvania, URL: http://www.cbil.upenn.edu/tess/index.html.

Heinrich, G. and Huynh, G. (Nov. 6, 2000) Genetic Analysis of Progressive Restriction of BDNF Gene Expression During Zebrafish Embryo Development. Annual Meeting of the Society for Neuroscience, New Orleans, Louisiana (Poster Presentation) 4 pages.

Huynh, G. and Heinrich, G. (Jul. 22-23, 2001) Regulation of Zebrafish BDNF Gene Expression Involves Both 5' and 3' Flanks. The 1st Bi-Annual West-Coast Regional Zebrafish Meeting, University of Washington, Seattle, Washington (18 pages).

Miles, C.G., Rankin, L, Smith, S.I., Niksic, M., Elgar, G., and Hastie, N.D. (2003) Faithful expression of a tagged Fugu WT1 protein from a genomic transgene in zebrafish: efficient splicing of pufferfish genes in zebrafish but not mice. Nucleic Acids Research, 31(11): 2795-2802.

Stuart, G.W., Vielkind, J.R., McMurray, J.V., and Westerfield, M. (1990) Stable lines of transgenic zebrafish exhibit reproducible patterns of transgene expression. Development, 109(3): 577-584.

Lum, T., G. Huynh, and G. Heinrich. (2001) Brain-derived neurotrophic factor and TrkB tyrosine kinase receptor gene expression in zebrafish embryo and larva. International Journal of Developmental Neuroscience, 19:569-587.

Russo-Neustadt A, T. Ha, R. Ramirez, and J.P. Kesslak. (2001) Physical activityantidepressant treatment combination: impact on brain-derived neurotrophic factor and behavior in an animal model.. Behaviour Brain Research, 120(1):87-95. BLTC Research. Web site: http://biopsychiatry.com/bdnf.htm. (Jan. 11, 2002).

U.S. Appl. No. 10/742,828, filed Dec. 23, 2003.

Heinrich, G., (2003) A novel BDNF gene promotor directs expression to skeletal muscle, BMC Neuroscience 2003, 4:11, 1-14.

Heinrich, G., and Pagtakhan C.J. (2004) Both 5' and 3' flanks regulate Zebrafish brain-derived neurotrophic factor gene expression, BMC Neuroscience 2004, 5:19, 20 pages (http://www.biomedcentral.com/1471-2202/5/19).

Williams et al., Transgenic animals in integrative biology: approaches and interpretations of outcome. J Appl. Physiol, 88: 119-1126, 2000.

Deiters et al., Conditional Transgene and Gene Targeting Methodologies in Zebrafish. Zebrafish, 3(4): 415-429, 2006.

Office Action dated Jan. 12, 2006 (vacated), in U.S. Appl. No. 10/742,828, filed Dec. 23, 2003.

Office Action dated Jan. 30, 2006, in U.S. Appl. No. 10/742,828, filed Dec. 23, 2003.

Office Action dated Oct. 10, 2006, in U.S. Appl. No. 10/742,828, filed Dec. 23, 2003.

Office Action dated Jun. 1, 2007, in U.S. Appl. No. 10/742,828, filed Dec. 23, 2003.

\* cited by examiner

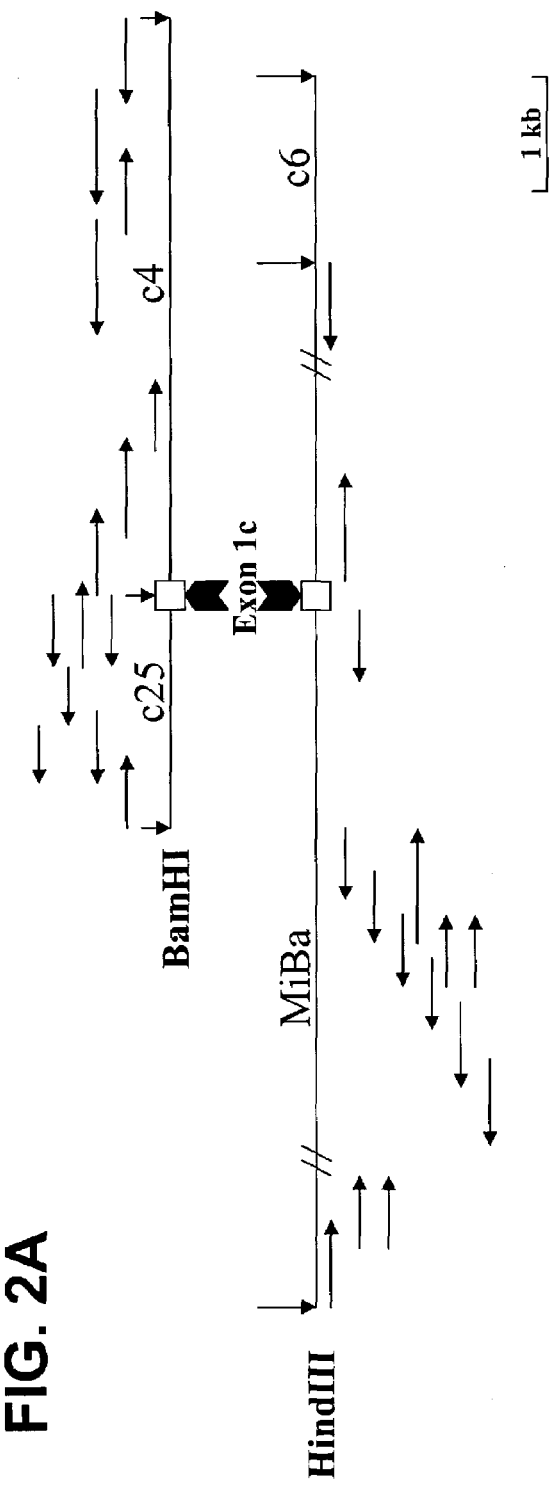
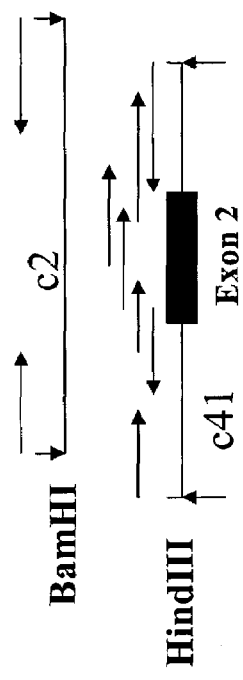
FIG. 2A
FIG. 2B

```
                                   Isl-1
     00001  ATGGGATCCATGTTGTTTTTGTGCTCCTAATGAGAAGCAGAGTGATTTAT
                  <----- CCWTNTTNNNW YY1
                        -----> TGTTGT  GR

PTF-1 beta            Isl-1              MEP-1
     00051  TTATGGGATTACCTAGCTGGAACAGCCCTAATGCACAGTGTGAGAGTGTG Zeste           HNF-1
     00101  CATGAGTGTATGTGTGTGTGTGCGCGCGCCTGTGTGTGTGTTTTACCT AP-1      Zeste
     00151  CTCTTGGAGTCATGTCGCTCAGTAATTGCTGATGCAACTCTTTGTCATCC AP-3                      PTF-1 beta
     00201  AGGGTTTGCCCTCTCCTCCTGTGAACCTATGGGATGAGTTATATTCATCT
                                              ----->TGAGTTA AP-1
                GR           PU.1
     00251  TGGCTTGTCCCTATAGGAGAGAGGAAGGGGACTGTAAGTGCCAGTATGTC Zeste  PRDI-BF1
     00301  AAAATGAGTGAAGGTGAAAGTATATTTGTATAATTTTATATTTGAAAGTG

IRF-1
     00351  TTCATGTGTAGCAGTGCAAAAAGGTTGAAGATGAGGTGACAAAGAAACAG

GATA-1           PU.1               HNF-1
     00401  AAAGGTGGAGATGGAAATAAGTAAAGAAAGAGGAAGTTTGTGTGTGTATG
                <----- TGTGCC GR
                                                              p300
     00451  TGTGCCAAGTGTGTGTATGTGTGTGTGAGAAGGCAAGGTGTTAGCATCCA

PR              Sp1                EF-2
     00501  CTCCCATGCTGGGAACAGCTAGGTTTGAAACCGCTCCACCTCATTACCTT
                -----> TCCCAT PTF-1 beta
                                              Pit-1A
     00551  ATGCAGGGAATAATCATCATCACTATACATAAAACTCATCAATATAAATC
                        <----- YTWWAaATAR CTF-1

GATA -1
     00601  TTGCACTGGACAAAATCCAAAAGCACTTGCAGCTTGGTGAAAGTATGGGG
                <----- YGGMNNNNNNgCCAA CTF-1

Isl-1                    PR,GR
     00651  CTAATGATGTGGTGAAGCATAGGGTGAAAGAACAAGGAATGCTTTCGCTA
                                              -----> AGGAATG MCBF

PPARalpha                        c-Myc
     00701  AACTTCTCCAGGAAGGTCACGTTAAATAAGAATTAAACAATAAAGCCGCA
     00751  GTTGAAGAGCAACATTATATCACCTCTATGTTTTTAAACATGTTTGACCA
     00801  TTTACAAAAATTAAACAAACCACTCCCAGTTATCAGAGGAATAGAACTGA
                    -----> ATTAAACAAg C/EBPbeta GR,PR                          NF-1
     00851  CACCGGAAGAACAATGAATAGTATTAAAATCAATGAACCAGCCAACATCT
                        -----> ATGAATA Pit-1a GR                      Zeste                Pit-1a
     00901  GGCACATAAGCTCCTTTGGCAGACGGGGGGCTCAAACCTGACAATAGTTT CR              ELP
     00951  AAAATATCACATACAGAGAAGACTAGGGAATAATAGGACCTTGATGTGGT
                    -----> ATCACA GCR
```

FIG. 5A

```
                              SRY              AP-1
01001  GGGAGCAAGGAGTGAGCTCTTTACTTTGAAGCTACCTTTGTGGAGTCACA
01051  ATTGCAAATATCAATTTCAGCAGATGATCTATAGTCTTGTCACAAAAAGG

HNF-1 Isl-1       Isl-1
01101  TGTTTCAGATTAACCTAATGGCTGTCCATTAGGATGCTGGTGCAGCATTT

Oct-1
01151  GTTCGCAGCTAAGACAGTGAATTTAAAGTGATTTAGATGGCAAATGTAAT
                          <----- AAGTGA IRF-1

IRF-1
01201  AACTTAAAACCATAATTTACAGTTTTACAGGCAAGTGAAATAACATATAA

NF-1/L
01251  ATTATAATTTTGCCAATTATACACAGCTGTAGCTACGTGAAACAAAACAG

GR/PR                         Oct-1
01301  GTGTTCACTAGAGCTAGGCTAATTTCTCATGTCTTTATACAAATAGTCAT
                    <----- KRGGCKRRK Sp-1
                         -----> ATTWNNNATK Oct-3

GR                  c-Ets-1
01351  GGAAAACAACACGAAACATCAAACCAAACGGATATATACATGAAACAGCA
            <----- ACAACA
                         <----- MRMMGGAWRY Elk-1

IRF-1       Hinf-3
01401  CAAGCATACGCATAAGCGTATGAGATTCACTTTGTATCAGCACACAAAGG
                         GC,PR ACAgAGGAAT ----->
                                  c-Ets-2 AAGGAA ----->

01451  AATCGTATTTTATATATACCTTCATCAGTAATGACGAAGAATGTGAACAA
                  AP-1
01501  AAATGTCAAAAGCCCACACTAACTCAGTGGTCGTCAGGAGAAGCCTGCTC

Sp1    Pit-1A
01551  GAGAAAAGAATGCGATGATTTAAAAATCGATGGGCGTTTAAAATCACCCC
                  -----> YtATTTWWAR MEF-2
                    AP-3 <----- GGgGTTTAAA
                   SREBP-1 ATCACCCCAc <-----

MEF-2
01601  AAGCCTCTATATGTCCAGGAATTAAAATAGGTTTCTGTCATATGTTGCTC
                     <----- MATNNWAAT Oct-3
                        <----- TAAAAT Pit-1a

NF-1
01651  GGTAAACGCCATAATAACACACTTTCCGGTTATTCGTTAGGAATAAGCAT c-Jun/ AP-1    CREB
01701  CTGAGGCTTCACTTGGTTGGCGCTCGCGCTTGAGTCACATGTTGCAACGT
                              -----> CACATG USF
                   C/EBPalpha -----> CAaGTTGCAAC
                        c-Jun <----- ACGTCA 01751  CACGGCAGTAGTTAGTTACTGTAGTCGCGAGGAATGAAGCCGTCATTTCA
                              -----> GAGGAA PU.1
                              -----> AGGAATG MCBF

01801  AGCTGGAGAGCTCTCTCAATGCGCACTACACTGCGAGCGCTCACCA...
```

FIG. 5B

```
   1  AGCGCCCAAT ACGCAAACCG CCTCTCCCCG CGCGTTGGCC GATTCATTAA
  51  TGCAGCTGGC ACGACAGGTT TCCCGACTGG AAAGCGGGCA GTGAGCGCAA
 101  CGCAATTAAT GTGAGTTAGC TCACTCATTA GGCACCCCAG GCTTTACACT
 151  TTATGCTTCC GGCTCGTATG TTGTGTGGAA TTGTGAGCGG ATAACAATTT
 201  CACACAGGAA ACAGCTATGA CCATGATTAC GCCAAGCTTG CATGCCTGCA
 251  GGTCGACTCT AGATTCTGAA TGGGATCCAT GTTGTTTTTG TGCTCCTAAT
 301  GAGAAGCAGA GTGATTTATT TATGGGATTA CCTAGCTGGA ACAGCCCTAA
 351  TGCACAGTGT GAGAGTGTGC ATGAGTGTAT GTGTGTGTGT GTGCGCGCGC
 401  CTGTGTGTGT GTTTTACCTC TCTTGGAGTC ATGTCGCTCA GTAATTGCTG
 451  ATGCAACTCT TTGTCATCCA GGGTTTGCCC TCTCCTCCTG TGAACCTATG
 501  GGATGAGTTA TATTCATCTT GGCTTGTCCC TATAGGAGAG AGGAAGGGGA
 551  CTGTAAGTGC GAGTATGTCA AAATGAGTGA AGGTGAAAGT ATATTTGTAT
 601  AATTTTATAT TTGAAAGTGT TCATGTGTAG CAGTGCAAAA AGGTTGAAGA
 651  TGAGGTGACA AAGAAACAGA AAGGTGGAGA TGGAAATAAG TAAAGAAAGA
 701  GGAAGTTTGT GTGTGTATGT GTGCCAAGTG TGTGTATGTG TGTGTGANAA
 751  GGCAAGGTGT TANCATCCAC TCCCATGCTG GAACAGCTA GGTTTGAAAC
 801  CGCTCCACCT CATTACCTTA TGCAGGGAAT AATCATCATC ACTATACATA
 851  AAACTCATCA ATATAAATCT TGCACTGGAC AAAATCCAAA AGCACTTGCA
 901  GCTTGGTGAA AGTATGGGGC TAATGATGTG GTGAANCATA GGGTGAAAGA
 951  ACAAGGAATG CTTTCGCTAA ACTTCTCCAG GAAGGTCACG TTAAATAAGA
1001  ATTAAACAAT AAAGCCGCAG TTGAAGAGCA ACATTATATC ACCTCTATGT
1051  TTTTAAACAT GTTTGACCAT TTACAAAAAT TAAACAAACC ACTCCCAGTT
1101  ATCAGAGGAA TAGAACTGAC ACCGGAAGAA CAATGAATAG TATTAAAATC
1151  AATGAACCAG CCAACATCTG GCACATAAGC TCCTTTGGCA GACGGGGGGC
1201  TCAAACCTGA CAATAGTTTA AAATATCACA TACAGAGAAG ACTAGGGAAT
1251  AATAGGACCT TGATGTGGTG GGAGCAAGGA GTGAGCTCTT TACTTTGAAG
```

FIG. 7A

```
1301  CTACCTTTGT GGAGTCACAA TTGCAAATAT CAATTTCAGC AGATGATCTA
1351  TAGTCTTGNC ACAAAAAGGT GTTTCAGATT AACCTAATGG CTGTCCATTA
1401  GGATGCTGGT GCAGCATTTG TTCGCAGCTA AGACAGTGAA TTTAAAGTGA
1451  TTTAGATGGC AAATGTAATA ACTTAAAACC ATAATTTACA GTTTTACAGG
1501  CAAGTGAAAT AACATATAAA TTATAATTTT GCCAATTATA CACAGCTGTA
1551  GCTACGTGAA ACAAAACAGG TGTTCACTAG AGCTAGGCTA ATTTCTCATG
1601  TCTTTATACA AATAGTCATG GAAAACAACA CGAAACATCA AACCAAACGG
1651  ATATATACAT GAAACAGCAC AAGCATACGC ATAAGCGTAT GAGATTCACT
1701  TTGTATCAGC ACACAAGGA ATCGTATTTT ATATATACCT TCATCAGTAA
1751  TGACGAAGAA TGTGAACAAA AATGTCAAAA GCCCACACTA ACTCAGTGGT
1801  CGTCAGGAGA AGCCTGCTCG AGAAAAGAAT GCGATGATTT AAAAATCGAT
1851  GGGCGTTTAA AATCACCCCA AGCCTCTATA TGTCCAGGAA TTAAAATAGG
1901  TTTCTGTCAT ATGTTGCTCG GTAAACGCCA TAATAACACA CTTTCCGGTT
1951  ATTCGTTAGG AATAAGCATC TGAGGCTTCA CTTGGTTGGC GCTCGCGCTT
2001  GAGTCACATG TTGCAACGTC ACGGCAGTAG TTAGTTACTG TAGTCGCGAG
2051  GAATGAAGCC GTCATTTCAA GCTGGAGAGC TCTCTCAATG CGCACTACAC
2101  TGCGAGCGCT CACCATGTCA TCCAACTGCT TCAACTCAAC TCCAAGGGA
2151  TCCCCGGGTA CCGGTCGCCA CCATGGTGAG CAAGGGCGAG GAGCTGTTCA
2201  CCGGGGTGGT GCCCATCCTG GTCGAGCTGG ACGGCGACGT AAACGGCCAC
2251  AAGTTCAGCG TGTCCGGCGA GGGCGAGGGC GATGCCACCT ACGGCAAGCT
2301  GACCCTGAAG TTCATCTGCA CCACCGGCAA GCTGCCCGTG CCCTGGCCCA
2351  CCCTCGTGAC CACCCTGACC TACGGCGTGC AGTGCTTCAG CCGCTACCCC
2401  GACCACATGA AGCAGCACGA CTTCTTCAAG TCCGCCATGC CCGAAGGCTA
2451  CGTCCAGGAG CGCACCATCT TCTTCAAGGA CGACGGCAAC TACAAGACCC
2501  GCGCCGAGGT GAAGTTCGAG GGCGACACCC TGGTGAACCG CATCGAGCTG
2551  AAGGGCATCG ACTTCAAGGA GGACGGCAAC ATCCTGGGGC ACAAGCTGGA
```

FIG. 7B

```
2601  GTACAACTAC AACAGCCACA ACGTCTATAT CATGGCCGAC AAGCAGAAGA
2651  ACGGCATCAA GGTGAACTTC AAGATCCGCC ACAACATCGA GGACGGCAGC
2701  GTGCAGCTCG CCGACCACTA CCAGCAGAAC ACCCCCATCG GCGACGGCCC
2751  CGTGCTGCTG CCCGACAACC ACTACCTGAG CACCCAGTCC GCCCTGAGCA
2801  AAGACCCCAA CGAGAAGCGC GATCACATGG TCCTGCTGGA GTTCGTGACC
2851  GCCGCCGGGA TCACTCTCGG CATGGACGAG CTGTACAAGT CCGGACTCAG
2901  ATCTAAGCTG AACCCTCCTG ATGAGAGTGG CCCCGGCTGC ATGAGCTGCA
2951  AGTGTGTGCT CTCCTGAGGA TCGATCCACC GGATCTAGAT AACTGATCAT
3001  AATCAGCCAT ACCACATTTG TAGAGGTTTT ACTTGCTTTA AAAAACCTCC
3051  CACACCTCCC CCTGAACCTG AAACATAAAA TGAATGCAAT TGTTGTTGTT
3101  AACTTGTTTA TTGCAGCTTA TAATGGTTAC AAATAAAGCA ATAGCATCAC
3151  AAATTTCACA AATAAAGCAT TTTTTCACT GCATTCTAGT TGTGGTTTGT
3201  CCAAACTCAT CAATGTATCT TAACGCGTAA ATTGTAAGCG TTAATATTTT
3251  GTTAAAATTC GCGTTAAATT TTTGTTAAAT CAGCTCATTT TTTAACCAAT
3301  AGGCCGAAAT CGGCAAAATC CCTTATAAAT CAAAAGAATA GACCGAGATA
3351  GGGTTGAGTG TTGTTCCAGT TTGGAACAAG AGTCCACTAT TAAAGAACGT
3401  GGACTCCAAC GTCAAAGGGC GAAAAACCGT CTATCAGGGC GATGGCCCAC
3451  TACGTGAACC ATCACCCTAA TCAAGTTTTT TGGGGTCGAG GTGCCGTAAA
3501  GCACTAAATC GGAACCCTAA AGGGAGCCCC CGATTTAGAG CTTGACGGGG
3551  AAAGCCGGCG AACGTGGCGA GAAAGGAAGG GAAGAAAGCG AAAGGAGCGG
3601  GCGCTAGGGC GCTGGCAAGT GTAGCGGTCA CGCTGCGCGT AACCACCACA
3651  CCCGCCGCGC TTAATGCGCC GCTACAGGGC GCGTCAGGTG CACTTTTCG
3701  GGGAAATGTG CGCGGAACCC CTATTTGTTT ATTTTTCTAA ATACATTCAA
3751  ATATGTATCC GCTCATGAGA CAATAACCCT GATAAATGCT TCAATAATAT
3801  TGAAAAAGGA AGAGTCCTGA GGCGGAAAGA ACCAGCTGTG AATGTGTGT
3851  CAGTTAGGGT GTGGAAAGTC CCCAGGCTCC CCAGCAGGCA GAAGTATGCA
```

FIG. 7C

```
3901  AAGCATGCAT CTCAATTAGT CAGCAACCAG GTGTGGAAAG TCCCCAGGCT
3951  CCCCAGCAGG CAGAAGTATG CAAAGCATGC ATCTCAATTA GTCAGCAACC
4001  ATAGTCCCGC CCCTAACTCC GCCCATCCCG CCCTAACTC CGCCCAGTTC
4051  CGCCCATTCT CCGCCCCATG GCTGACTAAT TTTTTTTATT TATGCAGAGG
4101  CCGAGGCCGC CTCGGCCTCT GAGCTATTCC AGAAGTAGTG AGGAGGCTTT
4151  TTTGGAGGCC TACTAGTCGG CCGTACGGGC CCTTTCGTCT CGCGCGTTTC
4201  GGTGATGACG GTGAAAACCT CTGACACATG CAGCTCCCGG AGACGGTCAC
4251  AGCTTGTCTG TAAGCGGATG CCGGGAGCAG ACAAGCCCGT CAGGGCGCGT
4301  CAGCGGGTGT TGGCGGGTGT CGGGGCTGGC TTAACTATGC GGCATCAGAG
4351  CAGATTGTAC TGAGAGTGCA CCATATGCGG TGTGAAATAC CGCACAGATG
4401  CGTAAGGAGA AAATACCGCA TCAGGCGGCC TTAAGGGCCT CGTGATACGC
4451  CTATTTTTAT AGGTTAATGT CATGATAATA ATGGTTTCTT AGACGTCAGG
4501  TGGCACTTTT CGGGGAAATG TGCGCGGAAC CCCTATTTGT TTATTTTTCT
4551  AAATACATTC AAATATGTAT CCGCTCATGA GACAATAACC CTGATAAATG
4601  CTTCAATAAT ATTGAAAAAG GAAGAGTATG AGTATTCAAC ATTTCCGTGT
4651  CGCCCTTATT CCCTTTTTTG CGGCATTTTG CCTTCCTGTT TTTGCTCACC
4701  CAGAAACGCT GGTGAAAGTA AAAGATGCTG AAGATCAGTT GGGTGCACGA
4751  GTGGGTTACA TCGAACTGGA TCTCAACAGC GGTAAGATCC TTGAGAGTTT
4801  TCGCCCCGAA GAACGTTTTC CAATGATGAG CACTTTTAAA GTTCTGCTAT
4851  GTGGCGCGGT ATTATCCCGT ATTGACGCCG GGCAAGAGCA ACTCGGTCGC
4901  CGCATACACT ATTCTCAGAA TGACTTGGTT GAGTACTCAC CAGTCACAGA
4951  AAAGCATCTT ACGGATGGCA TGACAGTAAG AGAATTATGC AGTGCTGCCA
5001  TAACCATGAG TGATAACACT GCGGCCAACT TACTTCTGAC AACGATCGGA
5051  GGACCGAAGG AGCTAACCGC TTTTTTGCAC AACATGGGGG ATCATGTAAC
5101  TCGCCTTGAT CGTTGGGAAC CGGAGCTGAA TGAAGCCATA CCAAACGACG
5151  AGCGTGACAC CACGATGCCT GTAGCAATGG CAACAACGTT GCGCAAACTA
```

FIG. 7D

```
5201  TTAACTGGCG AACTACTTAC TCTAGCTTCC CGGCAACAAT TAATAGACTG
5251  GATGGAGGCG GATAAAGTTG CAGGACCACT TCTGCGCTCG GCCCTTCCGG
5301  CTGGCTGGTT TATTGCTGAT AAATCTGGAG CCGGTGAGCG TGGGTCTCGC
5351  GGTATCATTG CAGCACTGGG GCCAGATGGT AAGCCCTCCC GTATCGTAGT
5401  TATCTACACG ACGGGGAGTC AGGCAACTAT GGATGAACGA AATAGACAGA
5451  TCGCTGAGAT AGGTGCCTCA CTGATTAAGC ATTGGTAACT GTCAGACCAA
5501  GTTTACTCAT ATATACTTTA GATTGATTTA AAACTTCATT TTTAATTTAA
5551  AAGGATCTAG GTGAAGATCC TTTTTGATAA TCTCATGACC AAAATCCCTT
5601  AACGTGAGTT TTCGTTCCAC TGAGCGTCAG ACCCCGTAGA AAAGATCAAA
5651  GGATCTTCTT GAGATCCTTT TTTTCTGCGC GTAATCTGCT GCTTGCAAAC
5701  AAAAAAACCA CCGCTACCAG CGGTGGTTTG TTTGCCGGAT CAAGAGCTAC
5751  CAACTCTTTT TCCGAAGGTA ACTGGCTTCA GCAGAGCGCA GATACCAAAT
5801  ACTGTCCTTC TAGTGTAGCC GTAGTTAGGC CACCACTTCA AGAACTCTGT
5851  AGCACCGCCT ACATACCTCG CTCTGCTAAT CCTGTTACCA GTGGCTGCTG
5901  CCAGTGGCGA TAAGTCGTGT CTTACCGGGT TGGACTCAAG ACGATAGTTA
5951  CCGGATAAGG CGCAGCGGTC GGGCTGAACG GGGGGTTCGT GCACACAGCC
6001  CAGCTTGGAG CGAACGACCT ACACCGAACT GAGATACCTA CAGCGTGAGC
6051  TATGAGAAAG CGCCACGCTT CCCGAAGGGA GAAAGGCGGA CAGGTATCCG
6101  GTAAGCGGCA GGGTCGGAAC AGGAGAGCGC ACGAGGGAGC TTCCAGGGGG
6151  AAACGCCTGG TATCTTTATA GTCCTGTCGG GTTTCGCCAC CTCTGACTTG
6201  AGCGTCGATT TTTGTGATGC TCGTCAGGGG GCGGAGCCTA TGGAAAAAC
6251  GCCAGCAACG CGGCCTTTTT ACGGTTCCTG GCCTTTTGCT GGCCTTTTGC
6301  TCACATGTTC TTTCCTGCGT TATCCCCTGA TTCTGTGGAT AACCGTATTA
6351  CCGCCTTTGA GTGAGCTGAT ACCGCTCGCC GCAGCCGAAC GACCGAGCGC
6401  AGCGAGTCAG TGAGCGAGGA AGCGGAAG
```

FIG. 7E

SEQUENCE LISTING

<160> NUMBER OF SEQ ID NOS: 8

<210> SEQ ID NO 1
<211> LENGTH: 1846
<212> TYPE: DNA
<213> ORGANISM: Danio rerio
<220> FEATURE:
<222> LOCATION:

<400> SEQUENCE: 1

```
atgggatcca tgttgttttt gtgctcctaa tgagaagcag agtgatttat         50
ttatgggatt acctagctgg aacagccta atgcacagtg tgagagtgtg         100
catgagtgta tgtgtgtgtg tgtgcgcgcg cctgtgtgtg tgttttacct         150
ctcttggagt catgtcgctc agtaattgct gatgcaactc tttgtcatcc         200
agggtttgcc ctctcctcct gtgaacctat gggatgagtt atattcatct         250
tggcttgtcc ctataggaga gaggaagggg actgtaagtg cgagtatgtc         300
aaaatgagtg aaggtgaaag tatatttgta taattttata tttgaaagtg         350
ttcatgtgta gcagtgcaaa aaggttgaag atgaggtgac aaagaaacag         400
aaaggtggag atggaaataa gtaaagaaag aggaagtttg tgtgtgtatg         450
tgtgccaagt gtgtgtatgt gtgtgtgaga aggcaaggtg ttagcatcca         500
ctcccatgct gggaacagct aggtttgaaa ccgctccacc tcattacctt         550
atgcagggaa taatcatcat cactatacat aaaactcatc aatataaatc         600
ttgcactgga caaaatccaa aagcacttgc agcttggtga aagtatgggg         650
ctaatgatgt ggtgaagcat agggtgaaag aacaaggaat gctttcgcta         700
aacttctcca ggaaggtcac gttaaataag aattaaacaa taaagccgca         750
gttgaagagc aacattatat cacctctatg tttttaaaca tgtttgacca         800
tttacaaaaa ttaaacaaac cactcccagt tatcagagga atagaactga         850
caccggaaga acaatgaata gtattaaaat caatgaacca gccaacatct         900
ggcacataag ctcctttggc agacgggggg ctcaaacctg acaatagttt         950
```

```
aaaatatcac atacagagaa gactagggaa taataggacc ttgatgtggt          1000
gggagcaagg agtgagctct ttactttgaa gctacctttg tggagtcaca          1050
attgcaaata tcaatttcag cagatgatct atagtcttgt cacaaaaagg          1100
tgtttcagat taacctaatg gctgtccatt aggatgctgg tgcagcattt          1150
gttcgcagct aagacagtga atttaaagtg atttagatgg caaatgtaat          1200
aacttaaaac cataatttac agttttacag gcaagtgaaa taacatataa          1250
attataattt tgccaattat acacagctgt agctacgtga aacaaaacag          1300
gtgttcacta gagctaggct aatttctcat gtctttatac aaatagtcat          1350
ggaaaacaac acgaaacatc aaaccaaacg gatatataca tgaaacagca          1400
caagcatacg cataagcgta tgagattcac tttgtatcag cacacaaagg          1450
aatcgtattt tatatatacc ttcatcagta atgacgaaga atgtgaacaa          1500
aaatgtcaaa agcccacact aactcagtgg tcgtcaggaa aagcctgctc          1550
gagaaaagaa tgcgatgatt taaaaatcga tgggcgttta aaatcacccc          1600
aagcctctat atgtccagga attaaaatag gtttctgtca tatgttgctc          1650
ggtaaacgcc ataataacac actttccggt tattcgttag gaataagcat          1700
ctgaggcttc acttggttgg cgctcgcgct tgagtcacat gttgcaacgt          1750
cacggcagta gttagttact gtagtcgcga ggaatgaagc cgtcatttca          1800
agctggagag ctctctcaat gcgcactaca ctgcgagcgc tcacca          1846

<210> SEQ ID NO 2
<211> LENGTH: 6428
<212> TYPE: DNA
<213> ORGANISM: Artificial Sequence
<220> FEATURE:
<221> NAME/KEY: Unsure
<222> LOCATION: 748, 763, 936, 1359
<223> OTHER INFORMATION: Synthesized

<400> SEQUENCE: 2
agcgcccaat acgcaaaccg cctctccccg cgcgttggcc gattcattaa            50
tgcagctggc acgacaggtt cccgactgga aaagcgggca gtgagcgcaa           100
cgcaattaat gtgagttagc tcactcatta ggcaccccag gctttacact           150
ttatgcttcc ggctcgtatg ttgtgtggaa ttgtgagcgg ataacaattt           200
cacacaggaa acagctatga ccatgattac gccaagcttg catgcctgca           250
ggtcgactct agattctgaa tgggatccat gttgttttg tgctcctaat            300 gagaagcaga gtgatttatt tatgggatta cctagctgga acagccctaa           350
tgcacagtgt gagagtgtgc atgagtgtat gtgtgtgtgt gtgcgcgcgc           400
ctgtgtgtgt gttttacctc tcttggagtc atgtcgctca gtaattgctg           450
atgcaactct ttgtcatcca gggtttgccc tctcctcctg tgaacctatg           500
ggatgagtta tattcatctt ggcttgtccc tataggagag aggaagggga           550
ctgtaagtgc gagtatgtca aaatgagtga aggtgaaagt atatttgtat           600
aattttatat ttgaaagtgt tcatgtgtag cagtgcaaaa aggttgaaga           650
tgaggtgaca agaaacagaa aaggtggaga tggaaataag taaagaaaga           700
ggaagtttgt gtgtgtatgt gtgccaagtg tgtgtatgtg tgtgtganaa           750
ggcaaggtgt tancatccac tcccatgctg ggaacagcta ggtttgaaac           800
```

```
cgctccacct cattacctta tgcagggaat aatcatcatc actatacata        850
aaactcatca atataaatct tgcactggac aaaatccaaa agcacttgca        900
gcttggtgaa agtatggggc taatgatgtg gtgaancata gggtgaaaga        950
acaaggaatg ctttcgctaa acttctccag gaaggtcacg ttaaataaga       1000
attaaacaat aaagccgcag ttgaagagca acattatatc acctctatgt       1050
ttttaaacat gtttgaccat ttacaaaaat taaacaaacc actcccagtt       1100
atcagaggaa tagaactgac accggaagaa caatgaatag tattaaaatc       1150
aatgaaccag ccaacatctg gcacataagc tcctttggca gacggggggc       1200
tcaaacctga caatagttta aaatatcaca tacagagaag actagggaat       1250
aataggacct tgatgtggtg ggagcaagga gtgagctctt tactttgaag       1300
ctacctttgt ggagtcacaa ttgcaaatat caatttcagc agatgatcta       1350
tagtcttgnc acaaaaaggt gtttcagatt aacctaatgg ctgtccatta       1400
ggatgctggt gcagcatttg ttcgcagcta agacagtgaa tttaaagtga       1450
tttagatggc aaatgtaata acttaaaacc ataatttaca gttttacagg       1500
caagtgaaat aacatataaa ttataatttt gccaattata cacagctgta       1550
gctacgtgaa acaaaacagg tgttcactag agctaggcta atttctcatg       1600
tctttataca aatagtcatg gaaaacaaca cgaaacatca aaccaaacgg       1650
atatatacat gaaacagcac aagcatacgc ataagcgtat gagattcact       1700
ttgtatcagc acacaaagga atcgtatttt atatatacct tcatcagtaa       1750
tgacgaagaa tgtgaacaaa aatgtcaaaa gcccacacta actcagtggt       1800
cgtcaggaga agcctgctcg agaaaagaat gcgatgattt aaaaatcgat       1850
gggcgtttaa aatcaccccca agcctctata tgtccaggaa ttaaaatagg      1900
tttctgtcat atgttgctcg gtaaacgcca taataacaca cttccggtt        1950
attcgttagg aataagcatc tgaggcttca cttggttggc gctcgcgctt       2000
gagtcacatg ttgcaacgtc acggcagtag ttagttactg tagtcgcgag       2050
gaatgaagcc gtcatttcaa gctggagagc tctctcaatg cgcactacac       2100
tgcgagcgct caccatgtca tccaactgct tcaactcaac tccaagggga       2150
tccccgggta ccgtcgcca ccatggtgag caagggcgag gagctgttca        2200
ccggggtggt gcccatcctg gtcgagctgg acggcgacgt aaacggccac       2250
aagttcagcg tgtccggcga gggcgagggc gatgccacct acggcaagct       2300
gaccctgaag ttcatctgca ccaccggcaa gctgcccgtg ccctggccca       2350
ccctcgtgac caccctgacc tacggcgtgc agtgcttcag ccgctacccc       2400
gaccacatga agcagcacga cttcttcaag tccgccatgc ccgaaggcta       2450
cgtccaggag cgcaccatct tcttcaagga cgacggcaac tacaagaccc       2500
gcgccgaggt gaagttcgag ggcgacaccc tggtgaaccg catcgagctg       2550
aagggcatcg acttcaagga ggacggcaac atcctggggc acaagctgga       2600
gtacaactac aacagccaca acgtctatat catggccgac aagcagaaga       2650
acggcatcaa ggtgaacttc aagatccgcc acaacatcga ggacggcagc       2700
gtgcagctcg ccgaccacta ccagcagaac acccccatcg gcgacggccc       2750
```

```
cgtgctgctg cccgacaacc actacctgag cacccagtcc gccctgagca       2800
aagaccccaa cgagaagcgc gatcacatgg tcctgctgga gttcgtgacc       2850
gccgccggga tcactctcgg catggacgag ctgtacaagt ccggactcag       2900
atctaagctg aaccctcctg atgagagtgg ccccggctgc atgagctgca       2950
agtgtgtgct ctcctgagga tcgatccacc ggatctagat aactgatcat       3000
aatcagccat accacatttg tagaggtttt acttgcttta aaaaacctcc       3050
cacacctccc cctgaacctg aaacataaaa tgaatgcaat tgttgttgtt       3100
aacttgttta ttgcagctta taatggttac aaataaagca atagcatcac       3150
aaatttcaca aataaagcat ttttttcact gcattctagt tgtggtttgt       3200
ccaaactcat caatgtatct taacgcgtaa attgtaagcg ttaatatttt       3250
gttaaaattc gcgttaaatt tttgttaaat cagctcattt tttaaccaat       3300
aggccgaaat cggcaaaatc ccttataaat caaagaata gaccgagata        3350 gggttgagtg ttgttccagt ttggaacaag agtccactat taaagaacgt       3400
ggactccaac gtcaaagggc gaaaaaccgt ctatcagggc gatggcccac       3450
tacgtgaacc atcacccta a tcaagttttt tggggtcgag gtgccgtaaa       3500
gcactaaatc ggaaccctaa agggagcccc cgatttagag cttgacgggg       3550
aaagccggcg aacgtggcga gaaaggaagg gaagaaagcg aaaggagcgg       3600
gcgctagggc gctggcaagt gtagcggtca cgctgcgcgt aaccaccaca       3650
cccgccgcgc ttaatgcgcc gctacagggc gcgtcaggtg cacttttcg        3700 gggaaatgtg cgcggaaccc ctatttgttt atttttctaa atacattcaa       3750
atatgtatcc gctcatgaga caataaccct gataaatgct tcaataatat       3800
tgaaaaagga agagtcctga ggcggaaaga accagctgtg gaatgtgtgt       3850
cagttagggt gtggaaagtc cccaggctcc ccagcaggca gaagtatgca       3900
aagcatgcat ctcaattagt cagcaaccag gtgtggaaag tccccaggct       3950
ccccagcagg cagaagtatg caaagcatgc atctcaatta gtcagcaacc       4000
atagtcccgc ccctaactcc gcccatcccg ccctaactc cgcccagttc        4050 cgcccattct ccgccccatg gctgactaat ttttttattt tatgcagagg       4100
ccgaggccgc ctcggcctct gagctattcc agaagtagtg aggaggcttt       4150
tttggaggcc tactagtcgg ccgtacgggc cctttcgtct cgcgcgtttc       4200
ggtgatgacg gtgaaaacct ctgacacatg cagctcccgg agacggtcac       4250
agcttgtctg taagcggatg ccgggagcag acaagcccgt cagggcgcgt       4300
cagcgggtgt tggcgggtgt cggggctggc ttaactatgc ggcatcagag       4350
cagattgtac tgagagtgca ccatatgcgg tgtgaaatac cgcacagatg       4400
cgtaaggaga aaataccgca tcaggcggcc ttaagggcct cgtgatacgc       4450
ctatttttat aggttaatgt catgataata atggtttctt agacgtcagg       4500
tggcactttt cggggaaatg tgcgcggaac ccctatttgt ttatttttct       4550
aaatacattc aaatatgtat ccgctcatga gacaataacc ctgataaatg       4600
cttcaataat attgaaaaag gaagagtatg agtattcaac atttccgtgt       4650
cgcccttatt cccttttttg cggcattttg ccttcctgtt tttgctcacc       4700
cagaaacgct ggtgaaagta aaagatgctg aagatcagtt gggtgcacga       4750
```

| | |
|---|---|
| gtgggttaca tcgaactgga tctcaacagc ggtaagatcc ttgagagttt | 4800 |
| tcgcccgaa gaacgttttc caatgatgag cacttttaaa gttctgctat | 4850 |
| gtggcgcggt attatcccgt attgacgccg ggcaagagca actcggtcgc | 4900 |
| cgcatacact attctcagaa tgacttggtt gagtactcac cagtcacaga | 4950 |
| aaagcatctt acgatggca tgacagtaag agaattatgc agtgctgcca | 5000 |
| taaccatgag tgataacact gcggccaact tacttctgac aacgatcgga | 5050 |
| ggaccgaagg agctaaccgc ttttttgcac aacatggggg atcatgtaac | 5100 |
| tcgccttgat cgttgggaac cggagctgaa tgaagccata ccaaacgacg | 5150 |
| agcgtgacac cacgatgcct gtagcaatgg caacaacgtt gcgcaaacta | 5200 |
| ttaactggcg aactacttac tctagcttcc cggcaacaat taatagactg | 5250 |
| gatggaggcg gataaagttg caggaccact tctgcgctcg gcccttccgg | 5300 |
| ctggctggtt tattgctgat aaatctggag ccggtgagcg tgggtctcgc | 5350 |
| ggtatcattg cagcactggg gccagatggt aagccctccc gtatcgtagt | 5400 |
| tatctacacg acggggagtc aggcaactat ggatgaacga atagacaga | 5450 |
| tcgctgagat aggtgcctca ctgattaagc attggtaact gtcagaccaa | 5500 |
| gtttactcat atatacttta gattgattta aaacttcatt tttaatttaa | 5550 |
| aaggatctag gtgaagatcc ttttgataa tctcatgacc aaaatcccctt | 5600 |
| aacgtgagtt ttcgttccac tgagcgtcag accccgtaga aaagatcaaa | 5650 |
| ggatcttctt gagatccttt ttttctgcgc gtaatctgct gcttgcaaac | 5700 |
| aaaaaaacca ccgctaccag cggtggtttg tttgccggat caagagctac | 5750 |
| caactctttt tccgaaggta actggcttca gcagagcgca gataccaaat | 5800 |
| actgtccttc tagtgtagcc gtagttaggc caccacttca agaactctgt | 5850 |
| agcaccgcct acatacctcg ctctgctaat cctgttacca gtggctgctg | 5900 |
| ccagtggcga taagtcgtgt cttaccgggt tggactcaag acgatagtta | 5950 |
| ccggataagg cgcagcggtc gggctgaacg ggggggttcgt gcacacagcc | 6000 |
| cagcttggag cgaacgacct acaccgaact gagataccta cagcgtgagc | 6050 |
| tatgagaaag cgccacgctt cccgaaggga gaaaggcgga caggtatccg | 6100 |
| gtaagcggca gggtcggaac aggagagcgc acgagggagc ttccaggggg | 6150 |
| aaacgcctgg tatctttata gtcctgtcgg gtttcgccac ctctgacttg | 6200 |
| agcgtcgatt tttgtgatgc tcgtcagggg ggcggagcct atggaaaaac | 6250 |
| gccagcaacg cggcctttt acggttcctg ccttttgct ggccttttgc | 6300 |
| tcacatgttc tttcctgcgt tatcccctga ttctgtggat aaccgtatta | 6350 |
| ccgcctttga gtgagctgat accgctcgcc gcagccgaac gaccgagcgc | 6400 |
| agcgagtcag tgagcgagga agcggaag | 6428 |

<210> SEQ ID NO 3
<211> LENGTH: 18
<212> TYPE: DNA
<213> ORGANISM: Artificial Sequence
<220> FEATURE:
<223> OTHER INFORMATION: Synthesized

<400> SEQUENCE: 3

```
acaggttaga agagtgat                                                     18

<210> SEQ ID NO 4
<211> LENGTH: 18
<212> TYPE: DNA
<213> ORGANISM: Artificial Sequence
<220> FEATURE:
<223> OTHER INFORMATION: Synthesized

<400> SEQUENCE: 4
cttaatggtc aatgtgca                                                     18

<210> SEQ ID NO 5
<211> LENGTH: 18
<212> TYPE: DNA
<213> ORGANISM: Artificial Sequence
<220> FEATURE:
<223> OTHER INFORMATION: Synthesized

<400> SEQUENCE: 5
gctcagtcat gggagtcc                                                     18

<210> SEQ ID NO 6
<211> LENGTH: 21
<212> TYPE: DNA
<213> ORGANISM: Artificial Sequence
<220> FEATURE:
<223> OTHER INFORMATION: Synthesized

<400> SEQUENCE: 6
atgaacgaac aggatggtca t                                                 21

<210> SEQ ID NO 7
<211> LENGTH: 15
<212> TYPE: DNA
<213> ORGANISM: Artificial Sequence
<220> FEATURE:
<223> OTHER INFORMATION: Synthesized

<400> SEQUENCE: 7
ctcaatgcgc actac                                                        15

<210> SEQ ID NO 8
<211> LENGTH: 18
<212> TYPE: DNA
<213> ORGANISM: Artificial Sequence
<220> FEATURE:
<223> OTHER INFORMATION: Synthesized

<400> SEQUENCE: 8
ggatcctttg gagttgag                                                     18
```

TRANSGENIC SCREEN AND METHOD FOR SCREENING MODULATORS OF BRAIN-DERIVED NEUROTROPHIC FACTOR (BDNF) PRODUCTION

CROSS-REFERENCE TO RELATED APPLICATIONS

The present application claims priority on prior U.S. Provisional Application Ser. No. 60/334,079, filed Nov. 30, 2001, and which is incorporated herein in its entirety by reference.

REFERENCE TO SEQUENCE LISTING

The present application incorporates by reference a file named: US 1325-02 Second Substitute Heinrich Sequence Listing, including SEQ ID NO: 1 to SEQ ID NO: 8, provided herewith in a computer readable form—on a diskette, created on Sep. 5, 2006 and containing 12,087 bytes. The sequence listing information recorded on the diskette is identical to the written (on paper) sequence listing provided herein.

BACKGROUND OF THE INVENTION

The present invention is generally directed to screening of genes or modulators, and more particularly to a transgenic screen for screening biological and chemical test substances for their ability to influence or modulate the production of BDNF in cells.

Brain-derived neurotrophic factor (BDNF) belongs to a group of nerve growth factors called neurotrophins (NT). The function of NTs includes fostering the growth and survival of neurons during development. In adult brains, NTs have an influence on neuronal excitability and, specifically, BDNF appears to regulate neuronal morphology and synaptogenesis. It is also known to exhibit neuroprotective effects in a range of central nervous system areas (Binder et al. 2001). BDNF has been shown to enhance motor neuron survival in several experimental animal models (Department of Neurology, Baylor College of Medicine 2001). Neurodegenerative diseases, such as Huntington's Disease, Parkinson's Disease and Alzheimer's Disease are expected to show abnormal BDNF expression. Enhancement of BDNF function is thought to be one of the mechanisms by which anti-depressants work (Russo-Neustadt et al. 2001) and, as such, might have a significant effect in treating depression.

It is believed that raising the level of BDNF production in the cells would be an effective method of treating various neurodegenerative disease conditions. The current screens for substances that modulate BDNF production are based on cell culturing. Therefore, the screens measure the level of BDNF that is secreted into the culture media and measure changes to this level caused by modulators. However, the screens do not measure the change that the modulating substances effect at the transcription level, and may therefore not be as specific in identifying the action of a modulator.

Other work has also linked the BDNF gene promoter to a fluorescent reporter gene that allows screening for agents which affect the reporter gene expression by affecting the BDNF promoter. One such method was in vitro, involving the culture of a transgenic cell line.

A second existing method involves transgenic mice expressing BDNF promoters linked to a reporter gene. Once again, these mice are able to give a readout on substances that modulate gene expression by affecting the BDNF promoter. However, the mice need to be sacrificed to measure the effect of the modulator, or at least a cell culture must be taken. In either case, the advantages of multiple series of dynamic screens on the same test stock are lost.

The conventional screens, methods, or in vitro tests measure BDNF production directly and do not identify the specific transcription mechanism by which production is increased. BDNF expression is the result of a complex process, however, with a number of regulatory ("promoter" or "cis-") genes regulating the transcription of the neurotrophic factor. The present invention allows screening for the expression of specific genetic segments, to allow researchers to identify factors that affect the activity of specific promoter genes.

OBJECTS AND SUMMARY OF THE INVENTION

The principal object of the present invention is to provide an isolated BDNF gene promoter.

An object of the present invention is to provide a nucleic acid construct.

Another object of the present invention is to provide a nucleic acid construct including a BDNF gene promoter and a fluorescent marker tag.

Yet another object of the present invention is to provide a zebrafish gene construct.

Still yet another object of the present invention is to provide a transgenic zebrafish line capable of expressing BDNF gene promoter.

Still yet another object of the present invention is to provide a cloned zebrafish genomic sequence.

Still yet another object of the present invention is to provide a cloned zebrafish genomic sequence which includes the 5' UT (untranslated) region of zebrafish BDNF cDNA with its associated promoter.

Still yet another object of the present invention is to provide a transgenic screen for in vivo screening of various biological, inorganic, and organic substances for their ability to modulate the production of BDNF at the transcription level of the BDNF gene in a living organism. The screen includes a zebrafish (*Danio rerio*) BDNF promoter sequence inserted upstream of a fluorescent marker gene so that the BDNF promoter is marked by fluorescence.

An additional object of the present invention is to provide a transgenic screen which can be used to identify gene targets for drugs for neurodegenerative diseases or to identify biological and chemical substances that directly upregulate BDNF promoters and may therefore have a therapeutic effect on neurodegenerative diseases. Since such substances may also have a neuroprotective effect on patients receiving chemotherapy, the indication thereof would be greatly useful and commercially desirable.

Yet an additional object of the present invention is to provide a transgenic screen which could be formatted for a high throughput screen (HTS).

A further object of the present invention is to provide a method of screening various biological and chemical substances or molecules for their capability to regulate BDNF production in a living organism.

Yet a further object of the present invention is to provide a method of screening various biological and chemical substances for regulation of BDNF production, which does not require cell cultures. Therefore, the effect of potential modulators or substances can be tested on multiple cell and tissue types. The BDNF gene transcription can be measured repeatedly, dynamically, serially, and in multiple screens in individual or groups of living embryos and larvae.

In summary, the main object of the present invention is to provide a transgenic screen and method for screening biological and chemical test substances or molecules for their ability to influence or modulate the production of BDNF in cells, which includes a fusion gene having a zebrafish BDNF gene fragment (promoter) and a fluorescent marker gene inserted downstream of the BDNF gene fragment. When the fusion gene is injected into a zebrafish embryo, the BDNF promoter causes the production of fluorescent protein in various cell types. The embryo is exposed to a test substance for determining the effect thereof on the production of the fluorescent marker protein.

BRIEF DESCRIPTION OF THE DRAWINGS

One of the above objects, novel features and advantages of the present invention will become apparent from the following detailed description of the preferred embodiment(s) of the invention, as illustrated in the drawings, in which:

FIGS. 2A-B illustrate zebrafish BDNF gene BamHI and HindIII subclones and sequencing strategy;

FIGS. 5A-B illustrate transcription factor recognition sites in the 5' flank/promoter region (SEQ ID NO: 1);

FIGS. 7A-E illustrate a nucleic acid sequence of a construct made in accordance with the present invention (SEQ ID NO: 2).

DETAILED DESCRIPTION OF THE INVENTION

Figure 1:
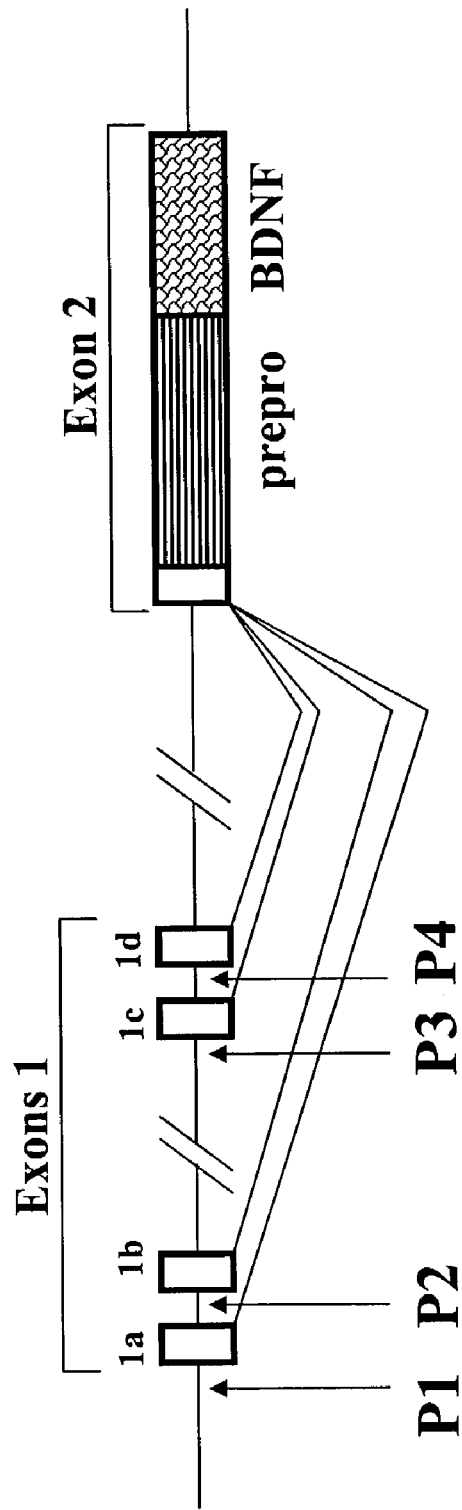
FIG. 1 illustrates organization of the mammalian BDNF gene.

The present invention illustrates a cloned zebrafish gene construct and a method of using the same in screening various biological and chemical substances or molecules for their capability to modulate the production of BDNF at the transcription level of the BDNF gene in a living organism.

Zebrafish are useful experimental organisms: small, about 3 cm long, the females can lay hundreds of eggs at weekly intervals. Since fertilization is external, the embryos can be manipulated easily as they are transparent, and examination can be made under the microscope (Wixon 2000). Mutagenesis screens are also easily achieved in the zebrafish, and large-scale projects of this nature have led to the production of huge numbers of mutant lines. Such populations can be useful in identifying genes that interact with the BDNF promoter and are consequently additional targets for modulating BDNF transcription (Huynh and Heinrich 2001).

Transgenic fish lines have been principally used within general scientific research in the analysis of promoter activity through reporter gene expression to identify cis-acting regulatory elements—i.e., the controlling effects of a regulatory gene on a structural gene (Dodd et al. 2000).

BDNF is a member of the neurotrophin family that also includes NGF (Levi-Montalcini, R. 1998, Levi-Montalcini, R. et al. 1995), NT-3 (Maisonpierre, P. C. et al. 1990, Maisonpierre, P. C. et al. 1991), NT-4/5 (Ip, N. Y. et al. 1992), NT-6 (Gotz, R. et al. 1994) and NT-7 (Nilsson, A. S. et al. 1998). BDNF is essential for the development and differentiation of specific sets of peripheral and central neuron in mammals (Alderson, R. F. et al. 1990, Hyman, C. et al. 1991, Johnson, J. E. et al. 1986, Sendtner, M. et al. 1992) and birds (Biffo, S. et al. 1994, Davies, A. M. et al. 1986, Frade, J. M. et al. 1997, Herzog, K. H. et al. 1994, Rodriguez-Tebar, A. and Barde, Y. A. 1988, Rodriguez-Tebar, A. et al. 1989). Like mammals and birds, the fishes possess a unique BDNF gene. Neither the structure nor the function of the fish BDNF gene are presently known.

To prepare tools for the molecular and cellular analysis of BDNF gene structure and function in the fish we used a recently cloned a zebrafish cDNA (Hashimoto, M. and Heinrich, G. 1997). Using the cDNA as a probe, we examined expression of BDNF mRNA in the developing zebrafish embryo and 4 day old larva. We extended this analysis to the earliest stages of embryonic development (Lum and Heinrich, 2001). These analyses showed that, in contrast to mammals, in the zebrafish, BDNF and BDNF mRNA are present in the zygote, and thus, may have a role in stages of development that precede nervous system formation. In the four day old larva BDNF and BDNF mRNA are expressed in specific cells within muscle, heart, neuromast, ear, brain, and cartilage.

Here we report on the cloning and structural analysis of the zebrafish BDNF gene. We show that its intron/exon organization is similar to that of the mammalian BDNF gene. Our genomic clones include the 5' untranslated region of the previously cloned BDNF cDNA and its associated promoter. When linked to an enhanced green fluorescent protein (EGFP-F) reporter and injected into Zebrafish embryos, this promoter mediates expression in cell types that express the endogenous BDNF gene. Transgenic lines derived from these embryos will allow us to utilize mutagenesis to identify genes that regulate BDNF gene expression.

Materials and Methods

Genomic Library Screening

A genomic PAC (P1 Artificial Chromosome) library was screened by colony hybridization. The library had been constructed from erythrocyte genomic DNA by C. T. Amemiya. The genomic DNA was partially digested with MboI and ligated into the pCYPAC6 (PAC) vector. Colonies were microarrayed onto nylon filters by the Resource Center of the German Genome Project (Vente, A. et al. 1999, Zehetner, G. and Lehrach, H. 1994). Each 9+9 inch filter contains approximately 24,000 clones (12,000 uniques plus 1 set of duplicates). 4 filters were provided by RZPD GmbH and screened with a mixture of two digoxigenin-labeled BDNF probes. The probes were prepared and labeled by PCR in the presence of digoxigenin-11-dUTP using a previously cloned zBDNF cDNA as template. Probe1 was directed exclusively to the coding exon (exon 2, FIG. 1) and probe2 mainly to the 5' untranslated region which has sequence similarity to exon 1c of the rat BDNF gene (FIG. 1). The following oligonucleotides were used for PCR. Probe1: sense 5'-acaggttagaagagt-gat-3' (SEQ ID NO: 3) and antisense 5'-cttaatggtcaatgtgca-3' (SEQ ID NO: 4). Probe2: sense:5'-gctcagtcatgggagtcc-3' (SEQ ID NO: 5) and antisense 5'-atgaacgaacaggatggtcat-3' (SEQ ID NO: 6).

FIG. 1 illustrates organization of the mammalian BDNF gene. Boxes designate exons, and lines introns and flanking regions. Open boxes represent 5' untranslated regions. The arrows indicate the positions of the four promoters which are labeled P1-4. The first 4 exons are alternatively spliced to exon 2 such that BDNF mRNA always includes two exons and always contains exon 2. The first four exons are accordingly labeled 1a-d. The striped box is the translated region of exon 2 that encodes the entire BDNF precursor. The scaly box represents the 3' untranslated region.

Mapping and Sequencing of Genomic Subclones

Standard restriction enzyme and Southern blot analyses were applied. Sequencing was contracted out to Davis Sequencing. DNA sequencing at the company is performed using ABI Prism 377 DNA sequencers with the 96-lane upgrade. Southern blots were probed with digoxigenin-labeled probes 1 and 2. A third probe (probe3) was used to identify the BamHI subclone encoding the 5' end of exon 1c (FIG. 2A). FIG. 2B shows the subclones (c2 and c41) that contain the coding exon 2. The following oligonucleotides were used to prepare probe3: sense 5'-ctcaatgcgcactac-3' (SEQ ID NO: 7) and antisense 5'-ggatcctttggagttgag-3' (SEQ ID NO: 8).

FIGS. 2A-B illustrate zebrafish BDNF gene BamHI and HindIII subclones and sequencing strategy. Vertical arrows mark restriction sites. Horizontal arrows indicate the origin, length and direction of sequencing reactions.

FIG. 2A shows the subclones that contain exon 1c (c4, c25, and MiBa). It is noted that exon 1c has a BamHI site. The promoter and 5' flank are located in c25. The 3' end of exon 1c and the 5' end of intron 1c are in c4. The sequencing gaps in MiBa are indicated by pairs of slashes. The empty box represents exon 1c. The vertical block arrows point to exon 1c.

FIG. 2B shows the subclones (c2 and c41) that contain the coding exon 2. The black box designates exon 2.

Construction of Fusion Genes

Starting materials were the genomic subclones and a plasmid carrying EGFP-F (pEGFP-F from Clontech, Palo Alto, Calif.). EGFP-F is a derivative of GFP (green fluorescent protein) with enhanced fluorescence and a farnesylation signal at the COOH-terminal derived from the src protein, which anchors EGFP in the cell membrane. Standard methods of restriction enzyme digestion and ligation of selected fragments were applied. Junctions of heterologous fragments were sequenced to confirm correct construction of fusion genes.

Preparation of DNA and Microinjection of Embryos

Plasmids were digested with HindIII and StuI or MluI. The desired restriction fragments were purified by agarose gel electrophoresis. DNA was dissolved in 100 mM KCl at a concentration of 10-50 μg/ml. Phenol red was added to visualize injected DNA solution. DNA was injected into a blastomere or into the cytoplasmic stream below the blastomere(s) at the 2-8 cell stages. Embryos were enzymatically dechorionated with Pronase and extensively washed in embryo medium prior to injection Embryo medium=13 mM NaCl; 4.2 mM NaHCO3; 0.54 mM KCl; 0.025 mM Na2HPO4; 0.044 mM KH2PO4; 1.3 mM CaCl2; 1 mM MgSO4). Embryos were injected and maintained for 14 hpf on a bed of 0.7% agarose in embryo medium. Subsequently, they were placed into deionized water in clear plastic dishes for observation with a Zeiss IM fluorescent microscope or further growth.

Immunocytochemistry

Four (4) days old larvae were fixed in 4% paraformaldehyde. Whole mount embryos were stained with monoclonal Ab C-9 (Santa Cruz Biotech., Santa Cruz, Calif.), raised against a synthetic peptide representing the N-terminal 27 amino acids of human BDNF. Specifically bound Ab was visualized using the ABC system.

In Situ Hybridization

Twenty-four (24) hrs old larvae were fixed in 4% paraformaldehyde. Whole mount embryos were hybridized with a digoxigenin-labeled PCR-generated probe targeted to exon 2 (probe1). Specifically bound probe was visualized with anti-digoxigenin-Fab conjugated to alkaline phosphatase.

Results

Screening of PAC Library

Four (4) 4 filters obtained from the RZPD GmbH (www.rzpd.de) were screened. Each filter contained 12 000 unique clones and 12 000 duplicates. A mixture of two digoxigenin-labeled probes was used. Probe 1 was directed toward the untranslated region of the previously cloned BDNF cDNA, and probe 2 to the coding exon. Two of the 48, 000 clones screened hybridized to the mixture. They were named c206 and c241.

Restriction Enzyme and Southern Blot Hybridization Analysis

Figure 3:
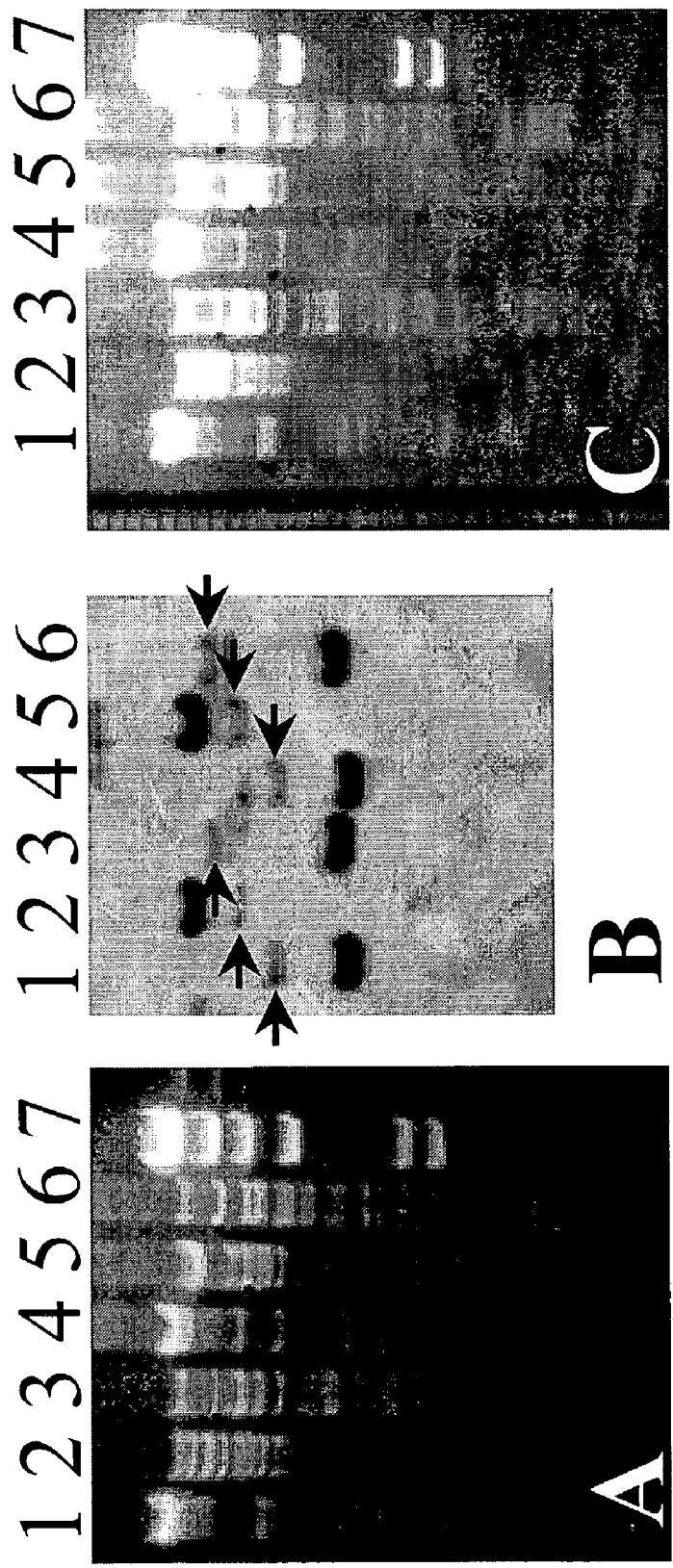
FIG. 3 illustrates restriction digest and southern blot hybridization analyses of genomic clones c206 and 241.

FIG. 3 illustrates restriction digest and southern blot hybridization analyses of genomic clones c206 and 241. Plasmid DNA was cut with various restriction enzymes and the digests were subjected to agarose gel electrophoresis in the presence of ethidium bromide. The gel was photographed and the DNA transferred to a nylon membrane. The membrane was probed sequentially with probe1 and probe2. Hybridized probe was visualized with an anti-digoxigenin FAb fragment conjugated to alkaline phosphatase and a chemiluminescent substrate. Panel A is underexposed to show the size marker (HindIII digest of Phage-lambda (lanes 7). Panel C is overexposed to show the smaller restriction fragments. Panel B shows the chemiluminogram. In all panels lanes 1-3 are c206 and lanes 4-6 c241. The DNA was digested with BamHI (lanes 1), HindIII (lanes 2) and EcoRI (lanes 3). The heavy bands in panel B represent hybridization with probe2. The light bands, marked with arrows, represent hybridization to probe1. It is noted that probe2 extends a short distance into exon 2 and therefore weakly hybridizes with DNA fragments containing exon 2.

The corresponding bacterial cultures were also obtained from the RZPD GmbH. Plasmid DNA was extracted from mini-cultures and analyzed by restriction enzyme digestion and southern blotting. The insert lengths were estimated from these digests as 100 kb for c206 and 80 kb for c241. FIG. 3 shows that there are restriction fragments that occur in both clones as well as those that are unique. The unique fragments add up to approximately 10 kb in c206 and 25kb for c241. The overlap is therefore approximately 65~70 kb.

Probe1 and probe2 hybridized to fragments that are common to both genomic clones supporting the conclusion that the genomic clones are authentic. On the other hand, probe1 and probe2 hybridized to different fragments in all three restriction enzyme digests in both clones, suggesting the 5' UT and coding exons are separated by a considerable distance. It is noted that probe2 overlaps to a small extent with exon 2 and, therefore, hybridizes weakly to the fragments recognized by probe1.

These analyses show that each of the two independent clones contains a complete transcription unit. Since the overlap is about 65 kb the transcription must be 65 kb or less. The human BDNF gene was found to be co-localized with 3 other genes on a 120 kb DNA fragment on chromosome 11p14 (Guillemot, F. et al. 1999).

Subcloning and Sequencing

The genomic clones c206 and c241 were digested with HindIII or BamHI and the mixture of fragments subcloned into the HindIII or BamHI sites of pEGFP-1 (Clontech). Non-fluorescent colonies were collected and screened by dot blot hybridization for subclones hybridizing to probe1, probe2, or probe3. One HindIII subclone hybridized to both probe2 and probe3. This clone was called MiBa. Another HindIII subclone hybridized to probe1, and was called c41. Three BamHI subclones hybridized to probe1, 2 or 3. They were called c2, c25, and c4, respectively. These clones were partially sequenced. (See FIGS. 2A-B for the sequencing strategies and portions that were sequenced.) The nucleotide sequences confirmed that we had cloned the zebrafish BDNF gene.

MiBa contains a 9 kb insert. c25 is completely embedded in MiBa. c4 overlaps with the 3' end of MiBa and contains an adjacent downstream 1.4 kb HindIII fragment. c41 and c2 contain 3 kb inserts and extensively overlap such that c2 extends only 250 bps farther 3' than c41. These mapping data are summarized in FIGS. 2A-B.

We have not yet mapped the relative positions of the HindIII or BamHI fragments that contain exon 1c and exon 2. Therefore, the size of intron 1c is not yet known.

RFLP

Figure 4:
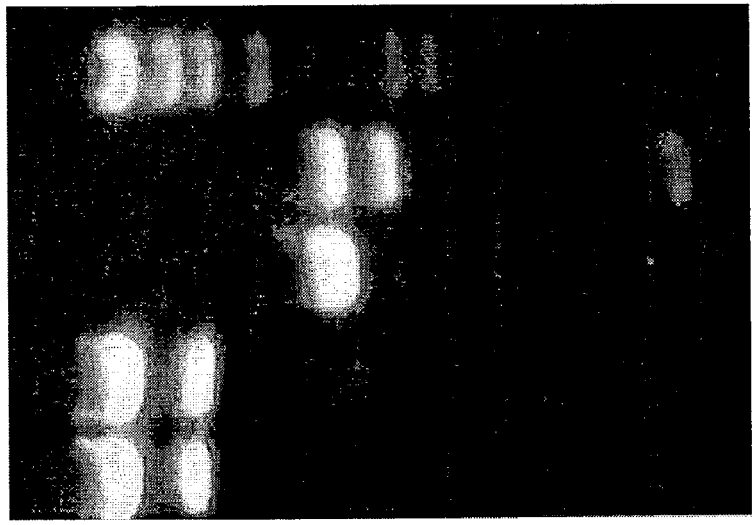
FIG. 4 illustrates apaI RFLP in BDNF gene coding exon.

FIG. 4 illustrates apaI RFLP in BDNF gene coding exon. Genomic subclone c41 and zBDNF cDNA clone 18.1 were digested with restriction enzymes and the fragments separated by agarose gel electrophoresis in the presence of ethidium bromide. The gel was photographed. Lanes 1-2: cDNA clone 18.1 cut with EcoRI (lane 1) and EcoRI/ApaI (lane 2). Lanes 3 and 4: genomic subclone c41 cut with HindIII (lane 3) and HindIII/ApaI (lane 4). Lane 5: Phage lambda HindIII digest.

The nucleotide sequence of c41 revealed an ApaI site in the prepro-region of the BDNF precursor that was not present in the previously cloned cDNA. The presence or absence of the ApaI site was confirmed by restriction analysis. c41 DNA, which contains the coding exon, and BDNF cDNA were cut with a single enzyme (HindIII and EcoRI, resp.) to release the cloned DNA. Aliquots of the digests were then cut with ApaI. The fragments were separated by agarose gel electrophoresis. FIG. 4 shows that the cDNA has no ApaI site and the genomic subclone c41 has a single one. As a result of the single nucleotide difference that abolishes the ApaI site the cDNA encodes a glutamic acid residue just downstream from the signal sequence of the BDNF precursor whereas the genomic clone encodes a Gln residue in the same position. The amino acid substitution alters the negative charge of the side-chain only two residues downstream from an Arg and therefore could be functionally significant. In any event, this RFLP will be useful in future mutagenesis screens when intragenic mutations must be distinguished from extragenic mutations by linkage analysis.

Alternate Promoters

The rat BDNF gene has four independently regulated promoters (see FIG. 1) (Bishop, J. F. et al. 1994, Hayes, V. Y. et al. 1997, Marmigere, F. et al. 1998, Metsis, M. et al. 1993, Nanda, S. and Mack, K. J. 1998, Shintani, A. et al. 1992, Timmusk, T. et al. 1994a, Timmusk, T. et al. 1993, Timmusk, T. et al. 1994b). The associated exons encode four 5' untranslated tracts which are alternately spliced to the coding exon to generate the mature BDNF mRNA transcripts, all of which encode the identical BDNF precursor. The alternate exons have been designated 1a-c and the coding exon has been exon 2 herein.

Nucleotide sequence comparison of the 5'UT of the previously cloned zebrafish BDNF cDNA with the rat BDNF gene revealed 67% identity with rat exon 1c (Hashimoto, M. and Heinrich, G. 1997). Moreover, in the zBDNF cDNA there was a sudden increase in similarity with the rat gene in the coding region at a point where the rat gene has an intron. This suggested that the zebrafish gene has an intron at the identical position. Sequence analysis of c41, which spans this region, confirmed the presence of an intron precisely where it occurs in the rat. Thus, the exon/intron structure of the BDNF gene is conserved.

In our in situ hybridization analyses of BDNF mRNA expression in 4 days old larvae, we had used probe1 and probe2 (Lum and Heinrich, 2001). The results showed a disparity between cells that hybridized to probe1 that is targeted exclusively to the coding exon (which is common to all BDNF transcripts) and probe2 that is targeted mainly to exon 1c. This disparity suggested that the zBDNF gene, like its rat counterpart, has multiple promoters. If their number and relative arrangement in the transcription unit were conserved we would expect an exon 1d about 500 bps downstream from exon 1c and a pair of exons 1a and b, also about 500 bps apart, located several kb upstream from exon 1c. Since a search through the nucleotide sequence bank at NCBI (National Center for Biological Information, Bethesda, Md.) for sequences similar to zebrafish exon 1c had identified rat exon 1c, we carried out similar searches using all sequences we had obtained from subclones MiBa, c4, and c25. However, none of the searches found any sequences that were related to the rat BDNF gene.

Promoter 3 Analysis

FIGS. 5A-B illustrate transcription factor recognition sites in the 5' flank/promoter region. The nucleotide sequence was searched for similarities with known transcription factor binding sites using TESS. The nucleotide sequences with similarity were boldfaced and the abbreviated transcription factor name was written above them. When there was overlap between sequences arrows below the sequences were used and the transcription factor names were written either to the left or right of the arrows. The cloned BDNF mRNA sequences are boldfaced, italicized and underlined. The following nucleotide designations are used in TESS: (AC) M; (AG) R; (AT) W; (CG) S; (CT) Y; (GT) K; (AGC) V; (ACT) H; (AGT) H; (CGT) D; (AGTC) X/N. For details on each of the transcription factors, TESS may be consulted.

c25 contains the 5' end of the previously cloned cDNA and therefore the associated promoter and 5' flank. To more precisely delineate the promoter region and to facilitate future functional analyses the entire clone was sequenced. The nucleotide sequence was scanned by computer for potential transcription factor binding sites using TESS ('TESS: Transcription Element Search Software on the WWW', Jonathan Schug and G. Christian Overton, Technical Report CBIL-TR-1997-1001-v0.0, of the Computational Biology and Informatics Laboratory, School of Medicine, University of Pennsylvania, 1997. As expected, a number of potential binding sites were found. The most relevant sites are shown in FIGS. 5A-B. The mammalian BDNF gene is known to be regulated by calcium (Bishop, J. F. et al. 1997, Finkbeiner, S. 2000, Sano, K. et al. 1996, Shieh, P. B. and Ghosh, A. 1999, Shieh, P. B. et al. 1998) and CREB (Tao, X. et al. 1998). Several AP-1 and a potential CREB recognition sequence were found close to the promoter suggesting the zebrafish may be regulated by similar upstream regulators.

Expression of Promoter 3 in Embryos

Figure 6A:
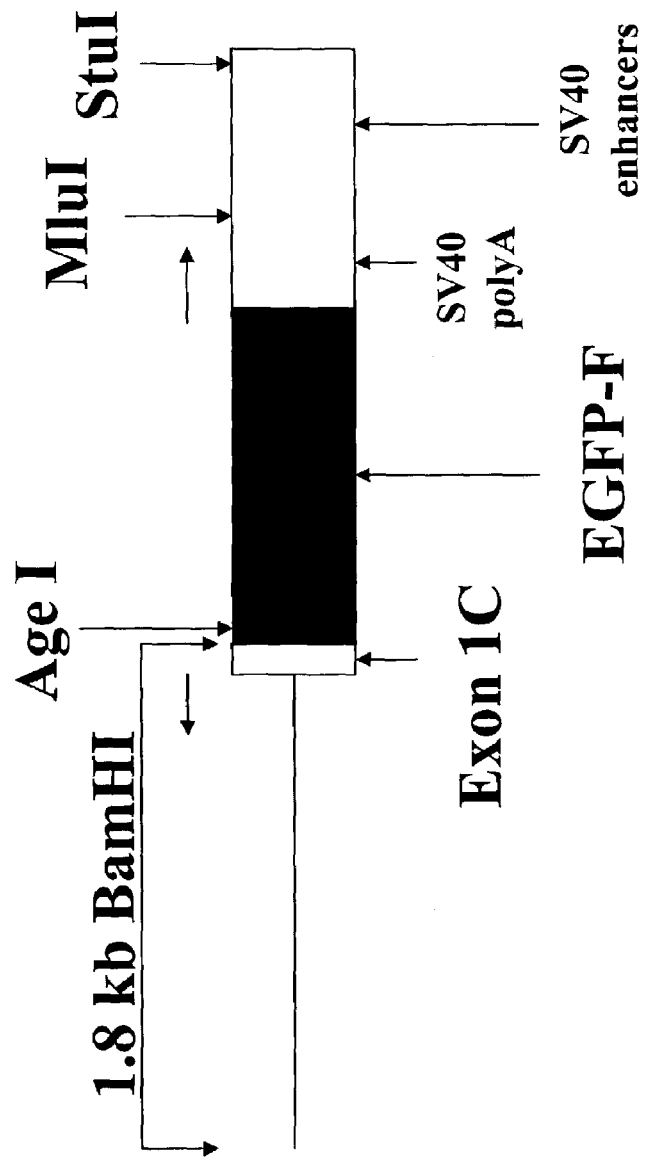
FIG. 6A illustrates an outline of BDNF/EGFP-F MiniExpress reporter construct of the invention.
Figure 6C:
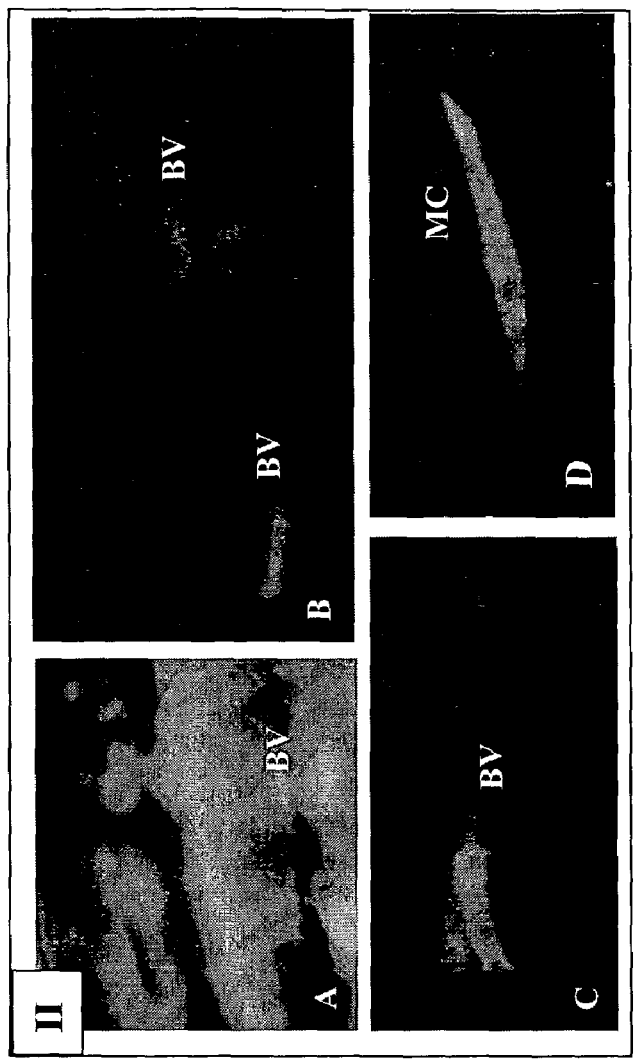
FIG. 6C (Panel II) (A-C) illustrates expression of BDNF/EGFP-F (MiniExpress) in blood vessels of 2-days old embryos.
Figure 6B:
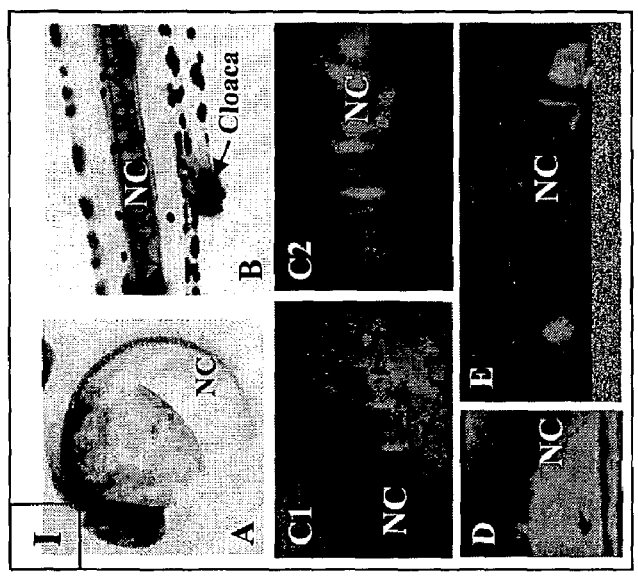
FIG. 6B (Panel I) (A-E) illustrates BDNF expression in notochord.

FIGS. 6A-C illustrate construction and expression of BDNF and BDNF/EGFP-F (MiniExpress) Fusion genes in zebrafish embryos and larvae.

FIG. 6A illustrates an outline of BDNF/EGFP-F MiniExpress reporter construct of the invention. The 5' end of exon 1c, consisting of 5' UT, is fused to the coding sequence of EGFP-F (black box). The 5' flank extends 1.7 kb upstream. The 3' end contains the SV40 polyadenylation upstream from the MluI site and SV40 enhancers between the MluI and StuI sites. Arrows indicate sequenced segments.

FIG. 6B. (Panel I) (A-E) illustrates BDNF expression in notochord. Panel IA illustrates BDNF mRNA visualized by in situ hybridization. The probe was a PCR-generated digoxigenin-labeled fragment of exon 2. Panel IB illustrates 4-days old larva. BDNF visualized by immunocytochemistry using MAb C-9 (Santa Cruz Biotech.). Panel IC1 illustrates 2-days old embryo injected with BDNF/EGFP-F (MiniExpress). Superimposed visible and fluorescent images. Panel IC2 illustrates fluorescent image of embryo shown in panel IC1. Panel ID illustrates 2-days old embryo injected with BDNF/EGFP-F (MiniExpress), fluorescent and visible images superimposed. Panel IE illustrates 2-days old embryo injected with BDNF/EGFP-F (MiniExpress), fluorescent image.

FIG. 6C (Panel II) (A-C) illustrates expression of BDNF/EGFP-F (MiniExpress) in blood vessels of 2-days old embryos. Panel IID illustrates expression of BDNF/EGFP-F (MiniExpress) in myocyte of trunk lateral myotome of 2-days old embryo. Panel III (A-C) illustrates expression of BDNF/EGFP-F (MiniExpress) in epithelial cells of 2-days old embryos. Panel IIIA1 is a lateral view, and panel IIIA2 a dorsal view of the same embryo. NC=notochord. BV=blood vessel.

To begin a functional analysis of promoter 1c, the insert of c25 was linked to the EGFP-F reporter. This reporter encodes an EGFP with a farnesylation signal at the 5' end. As a result, the EGFP becomes membrane anchored. In addition, the EGFP-F sequence is followed by SV40 polyA signals, mRNA 3' end and enhancers. We chose this reporter because it promised to be significantly more sensitive than EGFP. The resulting construct is shown in FIG. 6A and was called MiniExpress. Vector sequences and various SV40 sequences were removed prior to injection by digestion with StuI or MluI and agarose gel isolation of the desired fragments.

Embryos were dechorionated to facilitate injection of DNA into or close to the blastomeres at the 1-8 blastomere stages. However, even with injections at these early stages expression was highly mosaic, i.e. for any given cell type only a few cells expressed the reporter in any given injected embryo. For this reason, results are only reported for cell types that were seen to consistently express in >10 expressing embryos.

From the above, it can be observed that we have cloned a zebrafish genomic fragment that carries the BDNF coding exon and at least one functional promoter (FIG. 6A). Sequence analysis showed that the intron/exon organization of the zebrafish BDNF gene is identical to that of the mammalian BDNF gene. However, at this time we have identified with certainty only one promoter. Our in situ hybridization analyses with exon-specific probes showed that the exon 1c-specific probe hybridized to only a subset of BDNF mRNA positive cells (Lum and Heinrich, 2001). We also found several size classes of BDNF mRNA on Northern blot hybridization (Hashimoto, M. and Heinrich, G. 1997).

These findings suggest that the zebrafish BDNF gene has multiple promoters. Consistent with this possibility is the fact that promoter 1c expresses in only a subset of BDNF gene expressing cells. On the other hand, it is possible that the construct we examined lacks the cis regulatory elements that are required for expression in the additional cell types that express the endogenous BDNF gene. Again, this possibility are the results of preliminary experiments with constructs that extend farther upstream. Paradoxically, these constructs are expressed in fewer rather than more cell types than MiniExpress. The sequence analyses of MiBa and c4 are 90% complete. The remaining 10% could not be sequenced with the automated methods because they consist of small repetitive sequences and runs of adenosine and thymidine residues. They are thus unlikely to contain expressed exons. The sequenced regions of MiBa and c4 that contain potentially expressed exons together cover about 9 kb of genomic DNA. A BLAST search through the nucleotide sequence banks at NCBI for regions of similarity with the rat BDNF gene failed to find any. It is not clear whether any exons present in the sequenced regions are so dissimilar to their rat counterparts that they cannot be detected by the BLAST search engine, whether they are located farther away, or whether the zebrafish BDNF gene simply does not possess multiple promoters. The question of multiple promoters can be addressed experimentally by rapid amplification of cDNA ends (RACE).

The strong expression of BDNF mRNA in cartilage we had observed in our previous in situ hybridization and immunocytochemical analyses was originally somewhat unexpected (Lum and Heinrich, 2001). The expression of MiniExpress in the notochord that we observed in transiently transgenic embryos here are consistent with these data. The early and strong expression of the BDNF gene suggests an important function in skeleton development. The mammalian BDNF gene is also strongly expressed in cartilage and bone, but its function in these tissues is unknown.

The mammalian BDNF gene utilizes two polyadenylation signals that are almost 4 kb apart (Timmusk, T. et al. 1994, Timmusk, T. et al. 1993a). As a result most BDNF expressing tissues contain a large 4 kb transcript. Timmusk et al. (Timmusk, T. et al. 1994b) showed that this transcript is relatively rare in polysomes compared with the shorter more abundant transcripts of 1.6 kb and thus appears not to be as efficiently translated. We have not observed an equivalent large BDNF mRNA on our Northern blots despite overexposure of the autoradiograms (Hashimoto, M. and Heinrich, G. 1997). The zebrafish BDNF gene, thus appears to utilize only a single polyadenylation signal which we have cloned and sequenced. The 3' UT of the more abundant 1.6 kb mammalian BDNF mRNA and of zebrafish BDNF mRNA are relatively short, consisting of <500 nucleotides. Interestingly, our BLAST searches found two segments, a 23 and a 42 nucleotide segment, in the 3'UT that are identical in mammalian and zebrafish BDNF messages, suggesting important functions. Indeed, Timmusk et al. (Timmusk, T. et al. 1995) reported that the cloned rat BDNF gene was only expressed cell-specifically in transgenic mice if the 3' flank was included. However, the fragment they used extended 4 kb downstream from the first polyadenylation signal to the second polyadenylation signal. Therefore, it is not clear whether it is the conserved sequences in the 3'UT of the shorter message that are responsible for the observed cell-specific expression or sequences located yet farther downstream, or both.

We used a reporter derivative of the enhanced green fluorescent protein, EGFP (Harvey, K. J. et al. 2001). A farnesylation signal at the COOH end of this modified EGFP anchors the reporter in the cell membrane. We found this reporter significantly more sensitive that the non-membrane bound EGFP. The membrane anchored EGFP outlines the entire cell membrane. As a result, the identification of the cell type expressing the reporter is greatly facilitated. It was readily possible to distinguish various types of neurons because cell bodies, dendrites and axons were all completely labeled and outlined. For example, primary motor neurons were immediately distinguishable from the primary sensory Rohon-Beard cells (Inoue, A. et al. 1994, Martin, S. C. et al. 1998).

The construct of the invention can be used to rapidly screen a number of substances for their ability to influence the production of BDNF in a living organism. The preferable living organism is a zebrafish embryo or fry. The zebrafish is altered genetically so it carries the new gene that it passes on to all its progeny. The new gene or construct is assembled by standard molecular biology methods. It has two main components: a portion of the zebrafish BDNF gene that controls transcription, i.e., the promoter, and another gene that encodes a protein which fluoresces under UV light. The single new gene derived from the two components is called a fusion gene or construct.

When the fusion gene is injected into a zebrafish embryo, the BDNF promoter portion causes the production of the fluorescent protein in various cell types. The amount of protein, and hence fluorescence, is dependent on the activity of BDNF promoter. One can then expose embryos or larvae that carry this fusion gene to any desired chemical or biological substance to measure the effect of the substance on the production of the FP. The observed fluorescence is a measure of activity of the zebrafish's own BDNF gene and, hence a measure of BDNF production in various organs of the zebrafish. Bu utilizing this kind of screen, one can discover substances that have the capability to modulate BDNF production.

FIGS. 7A-E illustrate a construct made in accordance with the present invention, wherein nucleotides 1 to 263, 2154 to 2172, and 4159 to 6428 represent vectors; nucleotides 2173 to 2967 represent a reporter; nucleotides 264 to 2035 represent 5' flank of zebrafish BDNF gene; nucleotides 2036 to 2063 represent a promoter of zebrafish BDNF gene; nucleotides 2064 to 2153 exon 1c (5' UT) of zebrafish BDNF gene; nucleotides 3001-4159 represent SV40 sequences. The fragment injected into zebrafish embryos for expression is represented by nucleotides 236 to 3223.

OPERATION

The main tool are transgenic fish lines that stably express BDNF gene promoters linked to a fluorescent protein reporter (BDNF/FP fusion genes) whose cellular levels can be measured using fluorescent imaging equipment.

In order to create transgenic zebrafish lines, the BDNF/FP fusion genes are constructed from cloned zebrafish BDNF gene promoters and various fluorescent protein (FP) (green, red, yellow or blue) reporters by standard methods. (The FPs are obtained from commercial sources, such as Clontech, Inc.) The fusion genes are sequenced to confirm their structure, and are then injected into zebrafish embryos at the 1-8 cell stage of embryonic development. Transgenic lines are derived from the founder embryos by standard breeding and analysis methods.

Embryos from transgenic lines are exposed to a test substance and the level of reporter FP is compared to controls using fluorescent imaging equipment and computer image analysis. The test substances are either dissolved in ambient water or injected into the yolk or cell mass. At larval stages, the test substances are dissolved in ambient water or injected into various body sites, such as organs, the stomach, or the blood stream. We observed expression in notochord, muscle, epithelial and endothelial cells of the 1 day old embryo in consonance with the endogenous gene.

The construct of the invention and additional constructs, in progress, will allow us to establish transgenic zebrafish lines that will permit direct and live visual observation of BDNF gene expression. Such lines will be useful for the identification of genes that regulate BDNF gene expression using mutagenesis. With a short-lived reporter, it will also be possible to observe "real-time" dynamic changes of BDNF gene transcription in response to various physiological and experimental stimuli in the nervous system of the developing zebrafish embryo.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

The following references, to the extent that they provide exemplary procedural or other details supplementary to those set forth herein, are specifically incorporated herein by reference.

Alderson, R. F., Alterman, A. L., Barde, Y. A. and Lindsay, R. M., (1990) Brain-derived neurotrophic factor increases survival and differentiated functions of rat septal cholinergic neurons in culture. Neuron, 5: 297-306.

Amgen-Regeneron Partners. (2001) Intrathecal and Subcutaneous BDNF not shown effective in ALS. MDA Research. (Jan. 11, 2002.)

Balbes, L. M., M. Cline, and D .D. Beusen. (2001) From target to drug in the virtual discovery lab. Drug Discovery and Development. April 2001.

Biffo, S., Dechant, G., Okazawa, H. and Barde, Y. A., (1994) Molecular control of neuronal survival in the chick embryo. EXS, 71:39-48.

Binder, D. K., S. D. Croll, C. M. Gall, and H. E. Scharfman. (2001) BDNF and epilepsy: too much of a good thing? Trends in Neurosciences, 24(1):47-53.

Bishop, J. F., Joshi, G., Mueller, G. P. and Mouradian, M. M., (1997) Localization of putative calcium-responsive regions in the rat BDNF gene. Brain Res Mol Brain Res 50 IP, 1-2:154-164.

Bishop, J. F., Mueller, G. P. and Mouradian, M. M., (1994) Alternate 5' exons in the rat brain-derived neurotrophic factor gene: differential patterns of expression across brain regions. Brain Res Mol Brain Res 26 IP, 1-2:225-232.

Cockett, M., N. Dracopoli, and E. Sigal. (2000) Applied genomics: integration of the technology within pharmaceutical research and development. Current Opinion in Biotechnology, 11:602-609.

Cohen, N., Abramov, S., Dror, Y., and Freeman, A. (2001) In vitro enzyme evolution: the screening challenge of isolating the one in a million. TRENDS in Biotechnology, 19(12):507-510.

Davies, A. M., Thoenen, H. and Barde, Y. A., (1986) The response of chick sensory neurons to brain-derived neurotrophic factor. J Neurosci, 6:1897-904.

Department of Neurology, Baylor College of Medicine. (2001) Brain-Derived Neurotrophic Factor (BDNF) (Jan. 11, 2002.)

Dodd, A., P. M. Curtis, L. C Williams, and D. R Love. (2000) Zebrafish: bridging the gap between development and disease. Human Molecular Genetics. 9(16): Review, 2443-2449.

Finkbeiner, S., (2000) Calcium regulation of the brain-derived neurotrophic factor gene. Cell Mol Life Sci 57 IP, 3:394-401.

Fox, S. J., M. A. Yund, and S. Farr-Jones. (2000) Assay innovations vital to improving HTS. Drug Discovery and Development. March 2000.

Frade, J. M., Bovolenta, P., Martinez-Morales, J. R., Arribas, A., Barbas, J. A. and Rodriguez-Tebar, A., (1997) Control of early cell death by BDNF in the chick retina. Development, 124:3313-20.

Gotz, R., Koster, R., Winkler, C., Raulf, F., Lottspeich, F., Schartl, M. and Thoenen, H., (1994) Neurotrophin-6 is a new member of the nerve growth factor family. Nature, 372:266-9.

Guillemot, F., Auffray, C. and Devignes, M. D., (1999) Detailed transcript map of a 810-kb region at 11p14 involving identification of 10 novel human 3' exons. Eur J Hum Genet 7 IP, 4:487-495.

Harvey, K. J., Lukovic, D. and Ucker, D. S., (2001) Membrane-targeted green fluorescent protein reliably and uniquely marks cells through apoptotic death. Cytometry, 43:273-8.

Hashimoto, M. and Heinrich, G., (1997) Brain-derived neurotrophic factor gene expression in the developing zebrafish. Int J Dev Neurosci, 15:983-97.

Haupts, U., M. Rudiger. and A. J. Pope. (2000) Macroscopic versus microscopic fluorescence techniques in (ultra)-high throughput screening. Drug Discovery Today: HTS Supplement, 1 (1). June 2000.

Hayes, V. Y., Towner, M. D. and Isackson, P. J., (1997) Organization, sequence and functional analysis of a mouse BDNF promoter. Brain Res Mol Brain Res 45 IP, 2:189-198.

Herzog, K. H., Bailey, K. and Barde, Y. A., (1994) Expression of the BDNF gene in the developing visual system of the chick. Development, 120:1643-9.

Hyman, C., Hofer, M., Barde, Y. A., Juhasz, M., Yancopoulos, G. D., Squinto, S. P. and Lindsay, R. M., (1991) BDNF is a neurotrophic factor for dopaminergic neurons of the substantia nigra. Nature, 350:230-2.

Huynh, G. and G. Heinrich. (2001) Brain-derived neurotrophic factor gene organization and transcription in the zebrafish embryo. International Journal of Developmental Neuroscience, 19:663-673.

Inoue, A., Takahashi, M., Hatta, K., Hotta, Y. and Okamoto, H., (1994) Developmental regulation of islet-1 mRNA expression during neuronal differentiation in embryonic zebrafish. Dev Dyn, 199:1-11.

Ip, N. Y., Ibanez, C. F., Nye, S. H., McClain, J., Jones, P. F., Gies, D. R., Belluscio, L., Le Beau, M. M., Espinosa R, 3.r., Squinto, S. P. and et, a.l., (1992) Mammalian neurotrophin-4: structure, chromosomal localization, tissue distribution, and receptor specificity. Proc Natl Acad Sci U S A, 89:3060-4.

Johnson, J. E., Barde, Y. A., Schwab, M. and Thoenen, H., (1986) Brain-derived neurotrophic factor supports the survival of cultured rat retinal ganglion cells. J Neurosci, 6:3031-8.

Levi-Montalcini, R., Dal Toso, R., della Valle, F., Skaper, S. D. and Leon, A., (1995) Update of the NGF saga. J Neurol Sci, 130:119-27.

Levi-Montalcini, R., (1998) The saga of the nerve growth factor. Neuroreport, 9:R71-83.

Lum, T., G. Huynh, and G. Heinrich. (2001) Brain-derived neurotrophic factor and TrkB tyrosine kinase receptor gene expression in zebrafish embryo and larva. International Journal of Developmental Neuroscience, 19:569-587.

Maisonpierre, P. C., Belluscio, L., Squinto, S., Ip, N. Y., Furth, M. E., Lindsay, R. M. and Yancopoulos, G. D., (1990) Neurotrophin-3: a neurotrophic factor related to NGF and BDNF. Science, 247:1446-51.

Maisonpierre, P. C., Le Beau, M. M., Espinosa R, 3.r., Ip, N. Y., Belluscio, L., de la, M. o. S., Squinto, S., Furth, M. E. and Yancopoulos, G. D., (1991) Human and rat brain-derived neurotrophic factor and neurotrophin-3: gene structures, distributions, and chromosomal localizations. Genomics, 10:558-68.

Marmigere, F., Rage, F., Tapia-Arancibia, L. and Arancibia, S., (1998) Expression of mRNAs encoding BDNF and its receptor in adult rat hypothalamus. Neuroreport 9 IP, 6:1159-1163.

Martin, S. C., Sandell, J. H. and Heinrich, G., (1998) Zebrafish TrkC1 and TrkC2 receptors define two different cell populations in the nervous system during the period of axonogenesis. Dev Biol, 195:114-30.

Metsis, M., Timmusk, T., Arenas, E. and Persson, H., (1993) Differential usage of multiple brain-derived neurotrophic factor promoters in the rat brain following neuronal activation. Proc Natl Acad Sci U S A 90 IP, 19:8802-8806.

Nanda, S. and Mack, K. J., (1998) Multiple promoters direct stimulus and temporal specific expression of brain-derived neurotrophic factor in the somatosensory cortex. Brain Res Mol Brain Res 62 IP, 2:216-219.

Nature America Inc. (2000) Targeting zebrafish. nature genetics, 26(2): 129-130.

Nasevicius, A., and Ekker, S. (2000) Effective targeted gene 'knockdown' in zebrafish. nature genetics, 26:216-220.

Nilsson, A. S., Fainzilber, M., Falck, P. and Ibanez, C. F., (1998) Neurotrophin-7: a novel member of the neurotrophin family from the zebrafish. FEBS Lett, 424:285-90.

Pickering, L. (2001) Developing Drugs to Counter Disease. Medical Chemistry, 44-47.

Reiss, T. (2001) Drug discovery of the future: the implications of the human genome project. Trends in Biotechnology, 19(12):496-499.

Rodriguez-Tebar, A. and Barde, Y. A., (1988) Binding characteristics of brain-derived neurotrophic factor to its receptors on neurons from the chick embryo. J Neurosci, 8:3337-42.

Rodriguez-Tebar, A., Jeffrey, P. L., Thoenen, H. and Barde, Y. A., (1989) The survival of chick retinal ganglion cells in response to brain-derived neurotrophic factor depends on their embryonic age. Dev Biol, 136:296-303.

Russo-Neustadt A, T. Ha, R. Ramirez, and J. P. Kesslak. (2001) Physical activity antidepressant treatment combination: impact on brain-derived neurotrophic factor and behavior in an animal model. Behavior Brain Research, 120(1):87-95. BLTC Research. (Jan. 11, 2002.)

Sano, K., Nanba, H., Tabuchi, A., Tsuchiya, T. and Tsuda, M., (1996) BDNF gene can Be activated by Ca2+ signals without involvement of de novo AP-1 synthesis. Biochem Biophys Res Commun 229 IP, 3:788-793.

Sendtner, M., Holtmann, B., Kolbeck, R., Thoenen, H. and Barde, Y. A., (1992) Brain-derived neurotrophic factor prevents the death of motoneurons in newborn rats after nerve section. Nature, 360:757-9.

Shieh, P. B. and Ghosh, A., (1999) Molecular mechanisms underlying activity-dependent regulation of BDNF expression. J Neurobiol 41 IP, 1:127-134.

Shieh, P. B., Hu, S. C., Bobb, K., Timmusk, T. and Ghosh, A., (1998) Identification of a signaling pathway involved in calcium regulation of BDNF expression. Neuron, 20:727-40.

Shintani, A., Ono, Y., Kaisho, Y. and Igarashi, K., (1992) Characterization of the 5'-flanking region of the human brain-derived neurotrophic factor gene. Biochem Biophys Res Commun 182 IP, 1:325-332.

Stainier, D. (2001) Zebrafish Genetics and Vertebrate Heart Formation. Nature Reviews, 2:39-48.

Tao, X., Finkbeiner, S., Arnold, D. B., Shaywitz, A. J. and Greenberg, M. E., (1998) Ca2+ influx regulates BDNF transcription by a CREB family transcription factor-dependent mechanism. Neuron 20 IP, 4:709-726.

Timmusk, T., Belluardo, N., Persson, H. and Metsis, M., (1994a) Developmental regulation of brain-derived neurotrophic factor messenger RNAs transcribed from different promoters in the rat brain. Neuroscience 60 IP, 2:287-291.

Timmusk, T., Lendahi, U., Funakoshi, H., Arenas, E., Persson, H. and Metsis, M., (1995) Identification of brain-derived neurotrophic factor promoter regions mediating tissue-specific, axotomy-, and neuronal activity-induced expression in transgenic mice. J Cell Biol, 128:185-99.

Timmusk, T., Palm, K., Metsis, M., Reintam, T., Paalme, V., Saarma, M. and Persson, H., (1993) Multiple promoters direct tissue-specific expression of the rat BDNF gene. Neuron 10 IP, 3:475-489.

Timmusk, T., Persson, H. and Metsis, M., (1994b) Analysis of transcriptional initiation and translatability of brain-derived neurotrophic factor mRNAs in the rat brain. Neurosci Lett 177 IP, 1-2:27-31.

Vente, A., Korn, B., Zehetner, G., Poustka, A. and Lehrach, H., (1999) Distribution and early development of microarray technology in Europe. Nat Genet, 22:22.

Wixon, J. (2000) Danio rerio, the zebrafish. Yeast, 17:225-231. (Sep. 19, 2001.)

Zehetner, G. and Lehrach, H., (1994) The Reference Library System—sharing biological material and experimental data. Nature, 367:489.

What is claimed is:

1. A fusion gene, comprising:
   the nucleotide sequence comprising nucleotides 236 to 3223 set forth in SEQ ID NO.: 2.
2. A plasmid comprising the fusion gene of claim 1.
3. An in vitro cell comprising the fusion gene of claim 1.
4. A non-naturally occurring nucleic acid construct, comprising:
   the nucleotide sequence as set forth in SEQ ID NO.: 2.
5. A plasmid comprising the construct of claim 4.
6. An in vitro cell comprising the construct of claim 4.

* * * * *